United States Patent [19]
Rodell et al.

[11] Patent Number: 5,599,912
[45] Date of Patent: Feb. 4, 1997

[54] COMPOUNDS AND METHODS FOR SUPPRESSING AN IMMUNE RESPONSE TO SULFOMETHOXOZALE CONTAINING SUBSTANCES

[75] Inventors: Timothy C. Rodell, Denver; Vidal De La Cruz, Westminster; Catherine McCall, Boulder; James K. Blodgett; Donald A. McLeod, both of Westminster, all of Colo.

[73] Assignee: Coretech, Inc., Denver, Colo.

[21] Appl. No.: 118,819

[22] Filed: Sep. 10, 1993

[51] Int. Cl.$^6$ .......... A61K 39/395; C13K 5/00; C13K 7/00; C07H 1/00
[52] U.S. Cl. .......... 534/751; 534/573; 536/123.13; 536/123.1
[58] Field of Search .......... 514/59, 58, 54, 514/150; 536/123.1, 123.13; 534/573, 753, 751

[56] References Cited

U.S. PATENT DOCUMENTS

| | | | |
|---|---|---|---|
| 5,126,131 | 6/1992 | Dintzis et al. | 424/88 |
| 5,276,013 | 1/1994 | Conrad et al. | 514/2 |

FOREIGN PATENT DOCUMENTS

| | | | |
|---|---|---|---|
| 90-11778 | 10/1990 | WIPO | 424/88 |

OTHER PUBLICATIONS

White et al, "Desensitization to trimethohprim sulfamethoxazole in patients with acquired immune deficiency syndrome and Pneumocystis carinii pneumonia," Annals of Allergy, vol. 62, Mar, 1989, pp. 177–179.

Tatake et al, "Synthesis and Characterization of Protein and Polylysine Conjugates of Sulfamethoxazole and Sulfanilic Acid for Investigation of Sulfonamide Drug Allergy," Bioconjugate Chem. 2, (1991) pp. 124–132.

Gruchalla et al, "Detection of human IgE to sulfamethoxazole by skin testing with sulfamethoxazoyl–poly–L–tyrosine", J. Allergy Clin. Immunol. Nov. 1991, pp. 784–792.

Bozzette et al, "A Randomized Trial of Three Antipneumocystis Agents in Patients with Advanced Human Immunodeficiency Virus Infection", The New England Journal of Medicine, vol. 332, No. 11, Mar. 16, 1995, pp. 693–699.

Carr et al, "Efficacy and safety of rechallenge with low–dose trimethoprim–sulphamethoxazole in previously hypersensitive HIV–infected patients," AIDS, vol. 7, No. 1, 1993, pp. 65–71.

Carr et al, "Clinical and Laboratory Markers of Hypersensitivity to Trimethoprim–Sulfametoxazole in Patient with Pneumocystis carinii Pneumonia and AIDS", JID 1993:167 (Jan.) pp. 180–185.

Carrington et al, "Studies of human IgE to a sulfonamide determinant", J. Allergy Clin. Immunol., vol. 79, No. 3, Mar. 1987, pp. 442–447.

Kobs–Conrad et al., in Proceedings of the Twelfth American Peptide Symposium, J. A. Smith and J. E. Rivier, eds. ESCOM, Leiden, 886 (1992).

Hahn et al, Science: (248), 1554 (1990).

Castellano et al, Jama, vol. 266, No. 6, pp. 820 to 824 (1991).

Wood et al, N.E.J. Med., vol. 327, No. 26, pp. 1853 to 1860 (1992).

*Primary Examiner*—Floyd D. Higel
*Attorney, Agent, or Firm*—Schwegman, Lundberg, Woessner & Kluth, P.A.

[57] ABSTRACT

The present invention provides methods of detecting and suppressing an undesired immune response, and agents suitable for use therein. More specifically, the present invention, provides agents and methods for their use, directed at detecting and suppressing an undesired immune response to compositions containing sulfamethoxazole.

7 Claims, 13 Drawing Sheets

1:10

1:100

1:1000

COMPOUNDS AND METHODS FOR SUPPRESSING AN IMMUNE RESPONSE TO SULFOMETHOXOZALE CONTAINING SUBSTANCES

FIELD OF THE INVENTION

The present invention relates, in general, to methods of detecting and suppressing an undesired immune response and to agents suitable for use therein. More specifically, the present invention relates to agents, and methods for their use, directed at detecting and suppressing an undesired immune response to compositions containing sulfamethoxazole.

BACKGROUND OF THE INVENTION

As a mechanism of self defense, animals have developed a complex series of responses to foreign materials, collectively called the immune system. Immune responses are generally advantageous (i.e., protective) by nature. However, in certain situations, the animal body produces an immune response that is undesirable. Normally, the immune system recognizes and reacts to a vast variety of molecules, or antigens. Appropriate immune responses include the inactivation and clearance of foreign agents (such as bacteria or viruses), and surveillance against internally arising anomalies such as tumors. Inappropriate or excessive activation of the immune system, however, can cause several classes of disease, notably autoimmune disease and allergy. Autoimmune disease occurs when the immune system recognizes integral body components as if they were foreign and attacks them accordingly. Allergies occur when essentially innocuous extrinsic antigens such as pollen, animal dander or drugs elicit characteristic Immunoglobulin E (IgE) antibodies. Disease symptoms may also be triggered by the presence of Immunoglobulin G (IgG) antibodies to extrinsic antigens (e.g., drugs). These symptoms arise when excessive amounts of these antigens are present in the body.

A small percentage of patients (approximately 3%) treated with sulfonamide drugs such as sulfamethoxazole (SMX) experience immunologically-mediated adverse reactions. These can range from mild symptoms such as urticaria or fever to life threatening reactions such as anaphylaxis.

In recent years, the number of patients reported to experience allergic reactions to sulfonamides has increased. This is believed to be largely due to the increasing numbers of acquired immuno-deficiency disease (AIDS) patients undergoing antibiotic treatment or prophylaxis for *Pneumocystis carinii* pneumonia (PCP). Before the advent of the AIDS epidemic, PCP was a rarely reported disease seen mostly in highly immunosuppressed individuals such as pediatric cancer patients or organ transplant patients. Between 1967 and the early 1990's the annual number of reported cases of PCP rose from 65 to more than 20,000, paralleling the advent of AIDS. Currently, PCP is the most commonly occurring opportunistic infection and cause of death in AIDS patients in the USA. The Center for Disease Control and Prevention has recommended that all human immuno-deficiency virus (HIV) positive individuals start continuous prophylaxis for PCP as soon as their CD4+ T cell count falls below 200 cells per microliter of blood. The most widely prescribed treatment is sulfamethoxazole-trimethoprim (SMX-TMP), but a substantial proportion (up to 60%) of patients experience adverse reactions to the SMX component. In a small minority (approximately 3%) of patients, these adverse reactions appear to be of the classical IgE-mediated type, but in the majority of cases the symptoms observed are more typical of an IgG-mediated syndrome. Individuals experiencing adverse reactions to SMX may be treated with other drugs, notably pentamidine or dapsone. However, the cost for these treatment regimens is higher, the efficacy lower, and patients may experience adverse reactions to the alternative drugs (Castellano et al. JAMA: (266), 820–24 (1991); Wood et al. N.E.J.Med.: (327), 1853–60 (1992)). SMX has the added advantage in that it is effective against *Toxoplasma gondii*, another serious opportunistic infection in AIDS patients, whereas the alternative drugs have no effect on *T. gondii*.

As an alternative to changing drugs, patients may be desensitized to SMX with standard desensitization protocols similar to those used for penicillin-allergic individuals. Such desensitization has been carried out with some success in patients allergic to SMX (White et al. Ann. Allergy: (62), 177–79 (1992); Finegold et al. J. Allergy Clin. Immunol.: (78), 905–08 (1986)). However, these desensitization regimens require great care and intensive monitoring to be safe and effective. In addition, any lapse in exposure to the drug in question (for example, through patient non-compliance) results in resensitization.

Individuals allergic to one drug have a higher than normal risk of developing sensitivity to other, often unrelated drugs. It would seem prudent, therefore, to treat the primary allergy itself, thus allowing utilization of the most effective course of therapy.

Patients at risk for developing allergic reactions to drugs (for example, those who have experienced previous reactions to the drug in question, or to other drugs), must be treated with great caution at the start of drug therapy. The ability to predict any given individual's antibody status (particularly with regard to IgE) and, hence, risk for adverse reactions, would be of great clinical utility. Although IgG antibody levels may be assessed accurately with standard ELISA techniques, these assays are time-consuming and cannot be used to determine IgE antibody levels accurately. The standard method for determining IgE status in patients is by intra-dermal or skin-prick testing. These tests are based on the ability of multivalent antigen to cross-link IgE molecules attached via a high affinity IgE receptor to the surface of mast cells present in the skin. Such receptor cross-linking triggers the mast cell to release vasoactive mediators such as histamine and serotonin, resulting in a classic wheal and flare reaction readily observable shortly after the injection. However, testing patients for SMX allergy by this means is not currently efficient or reliable as no suitable multivalent form of SMX is available. Injection of the monovalent drug may result in weak reaction, depending on the ability of metabolites of SMX to attach to proteins in the skin, thus forming multivalent arrays.

Thus, there exists a long-felt need for effective means of diagnosing, preventing and treating sensitization to SMX-containing compositions. Such a treatment should ideally remove the inappropriate B-cell response, rather than merely reducing the symptoms. The present invention satisfies this need and provides related advantages as well.

SUMMARY OF THE INVENTION

The present invention is related to methods for the detection and prevention or treatment of sensitization to SMX, and compositions useful in such methods which allow continued effective and inexpensive prophylaxis, with SMX against such conditions as opportunistic infections in, for example, AIDS patients.

It is a specific object of the present invention to provide SMX-specific immunosuppressive agents, i.e., agents capable of preventing the induction of antibodies to SMX, or effecting the elimination of an ongoing antibody response to SMX, without effecting other immune responses. Broadly defined, the agents of the invention comprise an inert pharmaceutically acceptable non-immunogenic scaffold to which there are covalently attached one or more SMX moieties so as to exert an SMX specific immunosuppressive effect. Such agents may be more specifically illustrated by the general formula (I):

$$R-[X-Y-Z]_n$$

where R is a scaffold molecule; X is a scaffold appendage moiety; Y is a linking entity; Z is an SMX moiety, and n is the substitution density, i.e., the number of SMX moieties covalently attached to the scaffold via the unit —X—Y—.

DETAILED DESCRIPTION OF THE INVENTION

Figure 1:
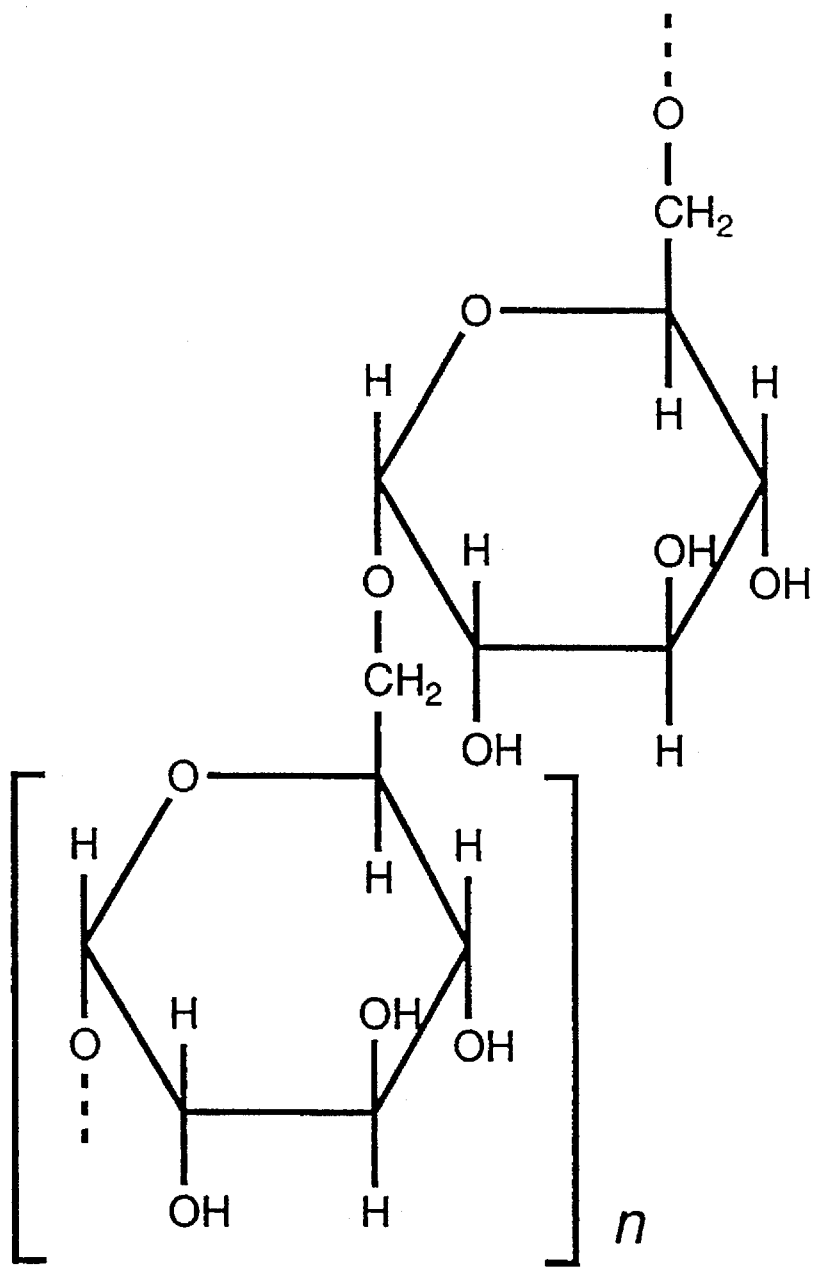
FIG. 1 illustrates the basic composition of a size-restricted dextran scaffold of average molecular weight 40K or 70K; n, the number of glucosyl residues comprising the dextran molecule, is approximately equal to 220 for a dextran of 40K average molecular weight, and 380 for a dextran of 70K average molecular weight.

The present invention relates generally to the suppression of undesired immune system activation, specifically B-cell activation, caused by the administration of SMX. More specifically, the invention involves the detection, suppression and elimination of undesired immune response to therapeutic SMX-containing compositions and their administration. The invention further relates to the prevention and treatment of antibody-mediated disease symptoms in individuals being treated with the drug and to the detection of antibodies to SMX in individuals about to be treated with SMX.

The present invention is based on the premise that the B cells of the immune system recognize foreign antigens in the context of physically constrained arrays. In order to stimulate the B cell component of the immune system, arrays must exceed a specific size (or geometry) and have a minimum number of physically accessible recognized structures, or epitopes, which are identical in nature (minimum valence). Once these two parameters are met or exceeded, the immune system will respond by the production of antibodies (IgM, and, with the help of T-cells, IgG, IgA, and/or IgE), by plasma cells, the progeny of antigen specific B-cells, and by the production of T-cell factors and/or activities (T-cell 'help', cytokines, cytoxicity, etc.). Further details of the methodology which forms the basis of the instant invention may be found, for example, in U.S. Pat. No. 5,126,131, incorporated herein by reference.

The role of T-cells in allergies, and in the autoimmune diseases systemic lupus erythematosus (SLE) and myasthenia gravis (MG), seems to be confined to helping the B-cells differentiate into plasma cells, the progeny of which produce the offending antibodies. In contrast to T-cell based approaches taken by many researchers, the antigen specific immunomodulation methodology upon which this invention relies, is focused on the parallel, and often primary pathway wherein antigen-specific B-cells, which are normally activated by SMX therapy, are specifically targeted for inactivation. With the inactivation of such antigen-specific B-cells, no auto-reactive or allergenic antibodies can be produced regardless of T-cell involvement, and the potential disease or undesired effect is thereby controlled or potentially eliminated.

The underlying method of the present invention allows for the design of a class of drugs that may block, with high specificity, the undesired immune system activation caused by SMX antigen. One skilled in the art will appreciate that antigens contain regions to which antibodies are made (called epitopes), with each epitope potentially binding to an immunoglobulin receptor on a B-cell. When the receptors on a B-cell are brought together by exposure to antigens in aggregates above a critical threshold number, the B-cell is believed to become activated. This threshold number of clustered receptors (the immunon) is consistent for the several antigens tested. The B-cell is not believed to be activated by an antigen if a limited number of receptors (i.e., less than the threshold number) are brought together on its surface.

Based on this model of activation, a class of compounds has been defined that can block B-cell activation by antigens in the following manner: B-cell epitopes of a target antigen are defined, and small sub-threshold numbers of these epitopes are then linked to an inert chemical backbone, i.e., to a scaffold molecule. It is believed that the compound can then tie up small clusters of receptors on B-cells and prevent a receptor cluster in excess of the critical threshold from forming. Thus, B-cells that recognize a given antigen will not be activated despite any continuing presence of antigen. Compounds based on such an activation model and methods of treatment involving such compounds can be made to specifically target diseases or conditions once causal antigens are identified.

As discussed previously, the number of patients with drug-related allergic responses has increased recently, due in part to increasing numbers of AIDS patients undergoing treatment for *Pneumocytis carinii* pneumonia. A high percentage of these patients have adverse reactions to sulfamethoxazole-trimethoprim (SMX-TMP) administration, the most widely prescribed treatment for PCP. By administering SMX-specific immunosuppressive agents, it has been found that B-cell activation by SMX antigens can be effectively blocked in animal models. Their use in humans may, therefore, allow continued treatment against the infectious agents.

As indicated, the compounds of the invention comprise one or more SMX moieties covalently bound to a non-immunogenic scaffold so as to provide an SMX-specific immuno-suppressive effect. The SMX-specific immunosuppressive agents of the invention may be illustrated by the following structure (I):

$$R\text{—}[X\text{—}Y\text{—}Z]_n$$

where R is a scaffold molecule; X is a scaffold appendage moiety; Y is a linking entity; Z is an SMX moiety, and n is the substitution density, i.e., the number of SMX moieties covalently attached to the scaffold via the unit —X—Y—.

The scaffolds R employed in the invention are non-immunogenic in nature and are freely soluble in physiologically acceptable aqueous buffers. A variety of different scaffolds R may be used although dextrans and peptides are generally preferred as discussed below.

The scaffold appendage moiety X may also take various forms as illustrated hereafter. In some instances, depending on the nature of the scaffold, the moiety X may be a group reactive with the linkage Y (e.g., amino) already present in the scaffold as conventionally available. However, with some scaffolds, it is preferred to add the moiety X to the scaffold to facilitate the linkage with the —Y—Z— component. In either case, the moiety X can be any linker which can be joined to the scaffold R through Y to permit stable linkage of the SMX moieties to the scaffold. Conveniently, but not necessarily, this may include amino, amido, amido polymethylene amino groups such as $$-\text{O}-\text{CH}_2-\overset{\overset{\text{O}}{\|}}{\text{C}}-\text{NH}-(\text{CH}_2)_p-\text{NH}-$$
where $p$ is 2–8, e.g., $$-\text{O}-\text{CH}_2-\overset{\overset{\text{O}}{\|}}{\text{C}}-\text{NH}-\text{CH}_2\text{CH}_2-\text{NH}-; \text{ or}$$

$$-\text{NH}-\overset{\overset{\text{O}}{\|}}{\text{C}}-(\text{CH}_2)_r-\text{NH}-$$
where $r$ is 1–8, e.g., $$-\text{NH}-\overset{\overset{\text{O}}{\|}}{\text{C}}-(\text{CH}_2)_5-\text{NH}-.$$

These are, however, only given as illustrations as other alternatives may also be used for, or as part of, the X moiety, e.g., ester groups, as replacements for NH.

Linking entity Y may be widely varied and may include, in whole or in part, for example, azobenzene groups (Class I), amide groups (Class II), succinimide based thioether groups (Class III) or non-succinimido- based thioether groups (Class IV) as shown by the following classes of SMX-specific immunosuppressive agents where R, X and Z have the meanings given above:

Class I $$R-X-\overset{\overset{O}{\|}}{C}-\underset{\underset{CH_2}{|}}{CH}-NH-\overset{\overset{O}{\|}}{C}-CH_3$$

with a phenyl ring bearing —N=N—Z and —OH substituents.

Class II $$R-X-\overset{\overset{O}{\|}}{C}-CH_2-CH_2-CH_2-\overset{\overset{O}{\|}}{C}-NH-Z$$

Class III $$R-X-\overset{\overset{O}{\|}}{C}-(CH_2)_3-N\underset{\text{(succinimide ring)}}{\overset{}{\diagdown}}-S-(CH_2)_2-NH-\overset{\overset{O}{\|}}{C}-(CH_2)_3-\overset{\overset{O}{\|}}{C}-NH-Z$$

Class IV

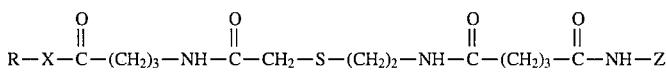

or

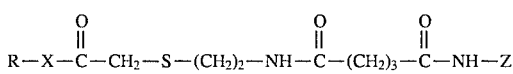

it being understood that Z is linked by Y to R-X- as follows:

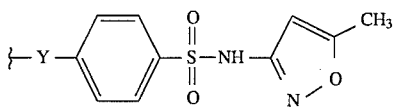

Only one Z is shown linked to R in the foregoing. However, it will be appreciated that the invention contemplates the use of multiple Z moieties linked to R to obtain the desired or optimum immunosuppressive effect. For example, n in Formula (I) above may vary over a substantial range, e.g., 2–70 or more, the number employed being dependent on such other factors as the nature of the suppressant.

As shown above, non-succinimide-based thioether units may be included in the linking entity Y to eliminate the succinimide-associated issues of chirality (i.e., mixture of enantiomers produced upon SMX attachment), hydrolysis (i.e., to open-chain compounds) and oxidative elimination (i.e., with release of SMX). Like their succinimide-based counterparts, non-succinimide-based thioether linking entities contain "masked" marker amino acids, i.e., amino acids not apparent without C-N bond cleavage, which would be liberated upon acid hydrolysis of the SMX-containing construct. These masked marked amino acids would aid in the determination or confirmation of the SMX substitution density. For example, the following could be expected:

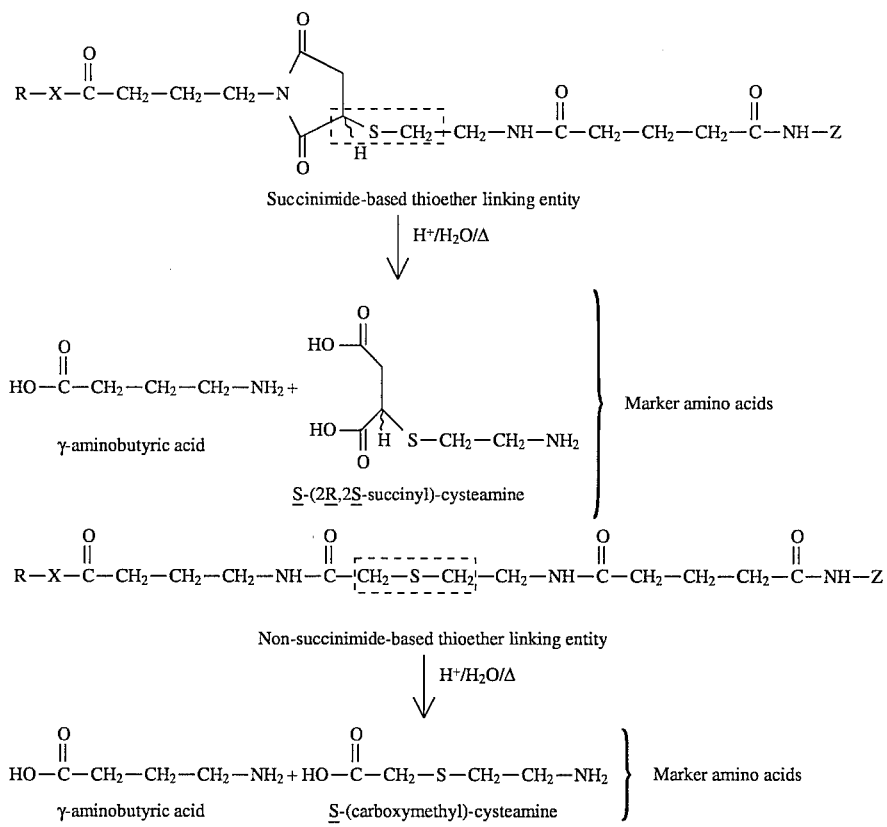

In this example, the two components of the SMX substitution density, namely, the amount of SMX covalently bound and the corresponding quantity of scaffold, would be proportional to the amounts of the recovered cysteamine derivative and γ-aminobutyric acid, respectively. This is provided that the thioether moiety (dotted line box) is generated concomitantly with formation of the linking entity during the course of SMX attachment to a scaffold molecule.

It will be apparent to those skilled in the art that linking entities other than those specified above may be appropriate for use in the covalent attachment of SMX moieties to a scaffold molecule. For example, marker amino acids such as β-alanine, e.g., on the scaffold side of the linker, and glycine, e.g., on the SMX side of the linker (or vice versa) are contemplated for inclusion in an amide linking entity as shown below $$R\text{---}\!\left[X\text{---}\overset{O}{\overset{\|}{C}}\text{---}(CH_2)_x\text{---}\!\overset{\;\;\;\;\;\;\;\;\;\;\;\;\;\;\;\;\;}{\left|NH\text{---}\overset{O}{\overset{\|}{C}}\right|}\!\text{---}(CH_2)_y\text{---}NH\text{---}\overset{O}{\overset{\|}{C}}\text{---}CH_2\text{---}CH_2\text{---}CH_2\text{---}\overset{O}{\overset{\|}{C}}\text{---}NH\text{---}Z\right]_n$$

x = 2, β-alanine residue    y = 1, glycine residue

Linking entities may be used to accommodate i) increased distance between the scaffold and the SMX moiety, a feature which may prove advantageous in an immunological setting and ii) amino acid analysis efforts directed toward establishing an unambiguous SMX substitution density. The two components of the substitution density would be proportional to the amounts of the recovered marker amino acids provided that the amide bond (dotted line box) is formed concomitantly with formation of the linking entity during the course of SMX attachment to a scaffold molecule. In addition, secondary amine-based linking entities may also be used according to this invention. Like their thioether and amide (bond) counterparts, secondary amine-based linking entities also contain "masked" marker amino acids which would be liberated upon acid hydrolysis (of the SMX-containing construct) and which would aid in the determination or confirmation of the SMX substitution density. For example, the following could be expected:

$$R\text{---}X\text{---}\overset{O}{\overset{\|}{C}}\text{---}CH_2\text{---}CH_2\text{---}CH_2\text{---}NH\text{---}\overset{O}{\overset{\|}{C}}\text{---}\!\overline{|CH_2\text{---}NH\text{---}CH_2|}\!\text{---}CH_2\text{---}NH\text{---}\overset{O}{\overset{\|}{C}}\text{---}CH_2\text{---}CH_2\text{---}CH_2\text{---}\overset{O}{\overset{\|}{C}}\text{---}NH\text{---}Z$$

Secondary amine-based thioether linking entity $$\Big\downarrow H^+/H_2O/\Delta$$

$$HO\text{---}\overset{O}{\overset{\|}{C}}\text{---}CH_2\text{---}CH_2\text{---}CH_2\text{---}NH_2 + HO\text{---}\overset{O}{\overset{\|}{C}}\text{---}CH_2\text{---}NH\text{---}CH_2\text{---}CH_2\text{---}NH_2 \Bigg\} \text{Marker amino acids}$$

γ-aminobutyric acid    N-(carboxymethyl)-ethylene diamine

In this example, the two components of the SMX substitution density would be proportional to the amounts of the recovered ethylene diamine derivative and γ-aminobutyric acid, respectively. This is provided that the secondary amine moiety (dotted line box) is generated concomitantly with formation of the linking entity during the course of SMX attachment to a scaffold molecule.

In one embodiment of the invention, R is a size-restricted dextran scaffold of average molecular weight ranging from 40K to 70K; X is a (dextran) glucosyl C2-, C3-, or C4

$$\text{---}O\text{---}CH_2\text{---}\overset{O}{\overset{\|}{C}}\text{---}NH\text{---}CH_2\text{---}CH_2\text{---}NH\text{-moiety;}$$

and Y and Z are as specified above.

The number of SMX moieties covalently attached to a given size-restricted dextran scaffold molecule may preferably be in the range of about 15–70 when R is dextran of 70,000 average molecular; weight. Alternatively, the average substitution density may preferably be in the range of about 7–30 when R is dextran of 40,000 average molecular weight.

Dextran, the structure of which is shown in FIG. 1, is an α1→6-linked polymer of D-glucose, and may be considered a "prototypical" scaffold R for a number of reasons: 1) it is freely soluble in physiologically acceptable aqueous buffers, 2) it can be modified for subsequent covalent attachment to SMX moieties using relatively simple chemistry, 3) it has been used in humans in gram quantities as a plasma expander with no significant toxicities, 4) it is commercially available in roughly size-fractionated bulk quantities at low cost and 5) there are no known mammalian dextranases. The latter point is particularly important since one of the primary considerations of this technology is that the SMX arrays be metabolically stable so that the desired anti-SMX antibody suppression may be effected in an experimental animal or human being.

In this embodiment of the invention, dextran scaffolds of lower average molecular weight (e.g., in the range of from 10K to 40K) are also contemplated. Scaffolds of molecular weight greater than 70K are contemplated as long as they remain non-immunogenic, i.e., possess the capacity for low substitution density of SMX moieties. Other size-restricted scaffolds in the 10K to 70K average molecular weight range such as polyacrylamide, Ficoll (Pharmacia—a non-ionic, synthetic sucrose polymer), carboxymethyl-cellulose, polyvinyl alcohol, poly(D-lysine) or poly(D-glutamic acid, D-lysine) are also within the scope of this invention. All such scaffolds are most preferably freely soluble in physiologically acceptable aqueous buffers when SMX moieties are attached and are non-immunogenic. Because an SMX-specific immunosuppressive agent based on a size-restricted scaffold such as dextran is an average molecular weight molecule, laser light scattering analysis may be employed for the purpose of establishing or confirming its structure, i.e., its SMX substitution density.

In the embodiment of the invention disclosed above, a size-restricted polymer was employed as the scaffold onto which SMX moieties were covalently arrayed. In a further embodiment of the invention, R is a valence-restricted scaffold. Unlike an SMX-specific immunosuppressive agent derived from a size-restricted scaffold, in which an average SMX substitution density is established necessarily as a result of the average molecular weight of the scaffold, the SMX substitution density of an SMX-specific immunosuppressive agent derived from a valence-restricted scaffold can be rigorously controlled with precisely defined chemistry. In addition, valence-restricted scaffolds have the general advantage of being defined molecular entities as opposed to size-restricted scaffolds which are average molecular weight molecules.

Figure 2A:
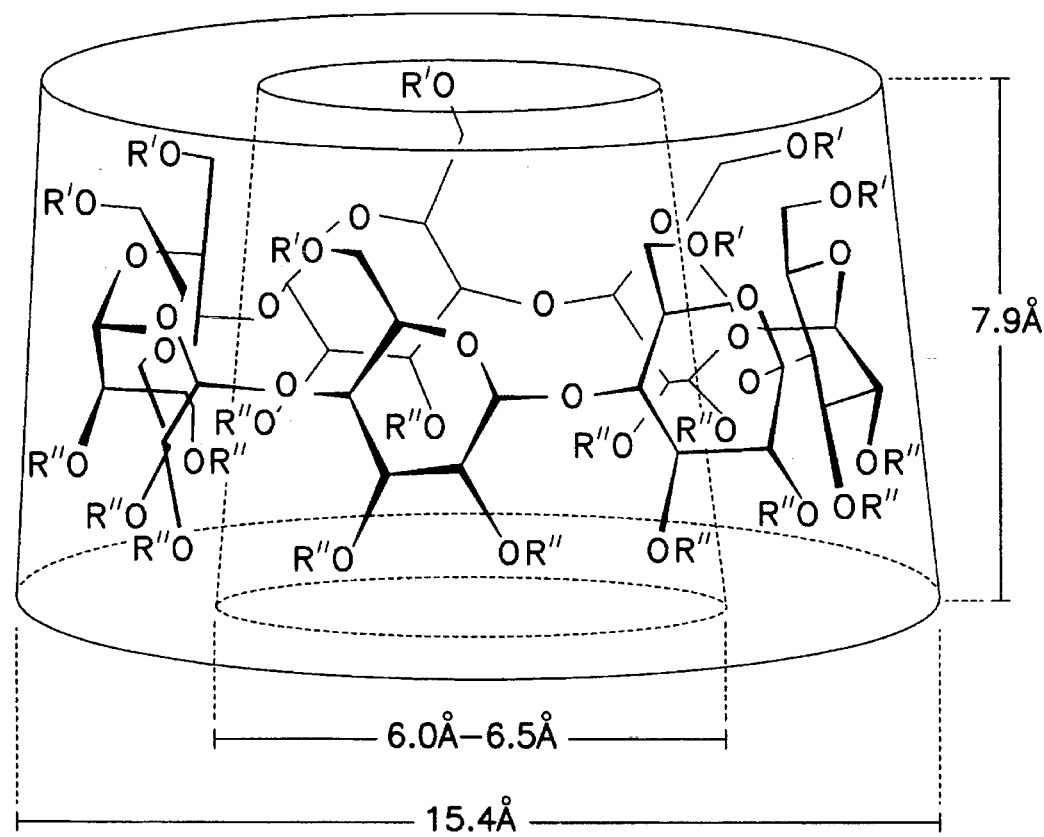
FIG. 2 illustrates the basic features of the three "natural" cyclodextrins, which represent one type of valence-restricted scaffold that may be used according to the present invention. The primary hydroxyl rim is comprised of the hydroxyls attached to the C6 carbons and the secondary hydroxyl rim is made up of hydroxyl groups attached to the C2 and C3 carbon atoms.
Figure 2B:
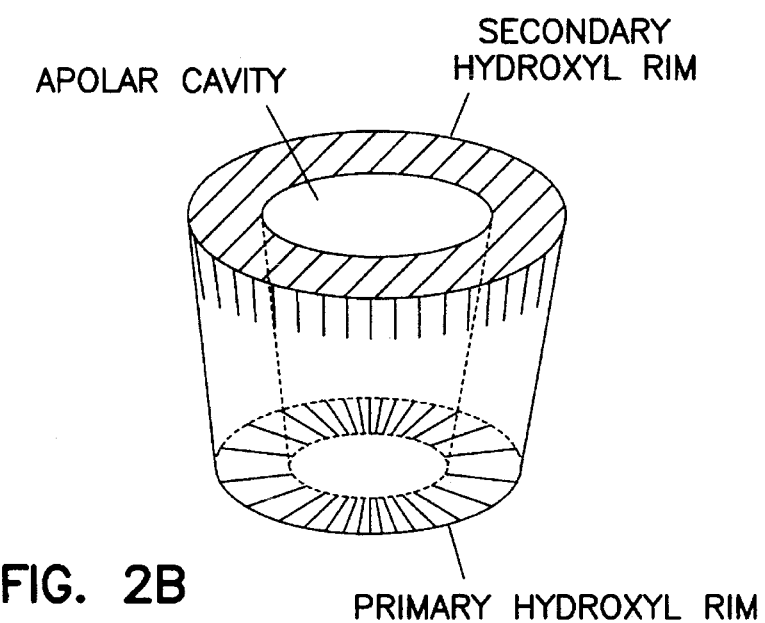

In a further specific embodiment of the invention, R is a valence-restricted β-cyclodextrin scaffold; X is a (β-cyclodextrin) glucosyl C6

$$-NH-\overset{O}{\underset{\|}{C}}-(CH_2)_5-NH-$$

moiety;
and Y and Z are as specified above.

β-cyclodextrin, the structure of which is shown in FIG. 2, is a cyclic oligosaccharide composed of 7 glucose units covalently linked through α1→4 glycosidic bonds. Using methods known in the art, the seven C6-primary hydroxyl groups can be selectively modified without concomitant modification of the C2- and C3-secondary hydroxyl groups that also exist in the scaffold molecule, resulting in a potential substitution density of 7 (Boger et al. Helvetica Chimica Acta: (61), 2910 (1978)). In other words, the number of SMX moieties that can be covalently attached to the β-cyclodextrin scaffold at the C6-position via the unit —X—Y— is 7. However, substitution densities greater or less than 7 are also possible by varying the functional nature of the scaffold appendage moiety and/or the linking entity.

In this embodiment of the invention, cyclodextrin scaffolds of lower molecular weight, such as α-cyclodextrin, and of higher molecular weight, such as γ-cyclodextrin, are also contemplated. As with the C6-primary hydroxyl groups of β-cyclodextrin, those of α- and γ-cyclodextrin may also undergo selective modification with chemical reagents to afford the corresponding number of glucosyl C6

$$-NH-\overset{O}{\underset{\|}{C}}-(CH_2)_5-NH-$$

moieties.

Thus, SMX-specific immunosuppressive agents based on these valence-restricted scaffolds, which are cyclic α1→4-linked oligosaccharides composed of 6 and 8 glucose units, respectively, possess potential SMX substitution densities of 6 and 8 under the conditions of this disclosure. It is preferred that the SMX-specific immunosuppressive agents incorporating the valence-restricted cyclodextrin scaffolds are freely soluble in physiologically acceptable aqueous buffers.

Regardless of the actual choice of cyclodextrin (α, β, or γ), its use as a valence-restricted scaffold produces a radially dispersed array of SMX moieties. This is in contrast to the linear array of SMX moieties that necessarily accompanies the use of a size-restricted scaffold such as dextran. Because an SMX-specific immunosuppressive agent based on a valence-restricted cyclodextrin scaffold is a defined molecular entity with a unique molecular weight, mass spectrometry may be employed for the purpose of confirming its structure, i.e., its SMX substitution density.

One skilled in the art will appreciate that β-cyclodextrin, and cyclodextrins in general, represent(s) only one of several types of valence-restricted scaffolds. In a further embodiment of the invention, R is a valence-restricted, peptide-based dendritic scaffold; X is a (peptide) α-amino (—NH—) moiety and Y and Z are as specified above.

Figure 3:
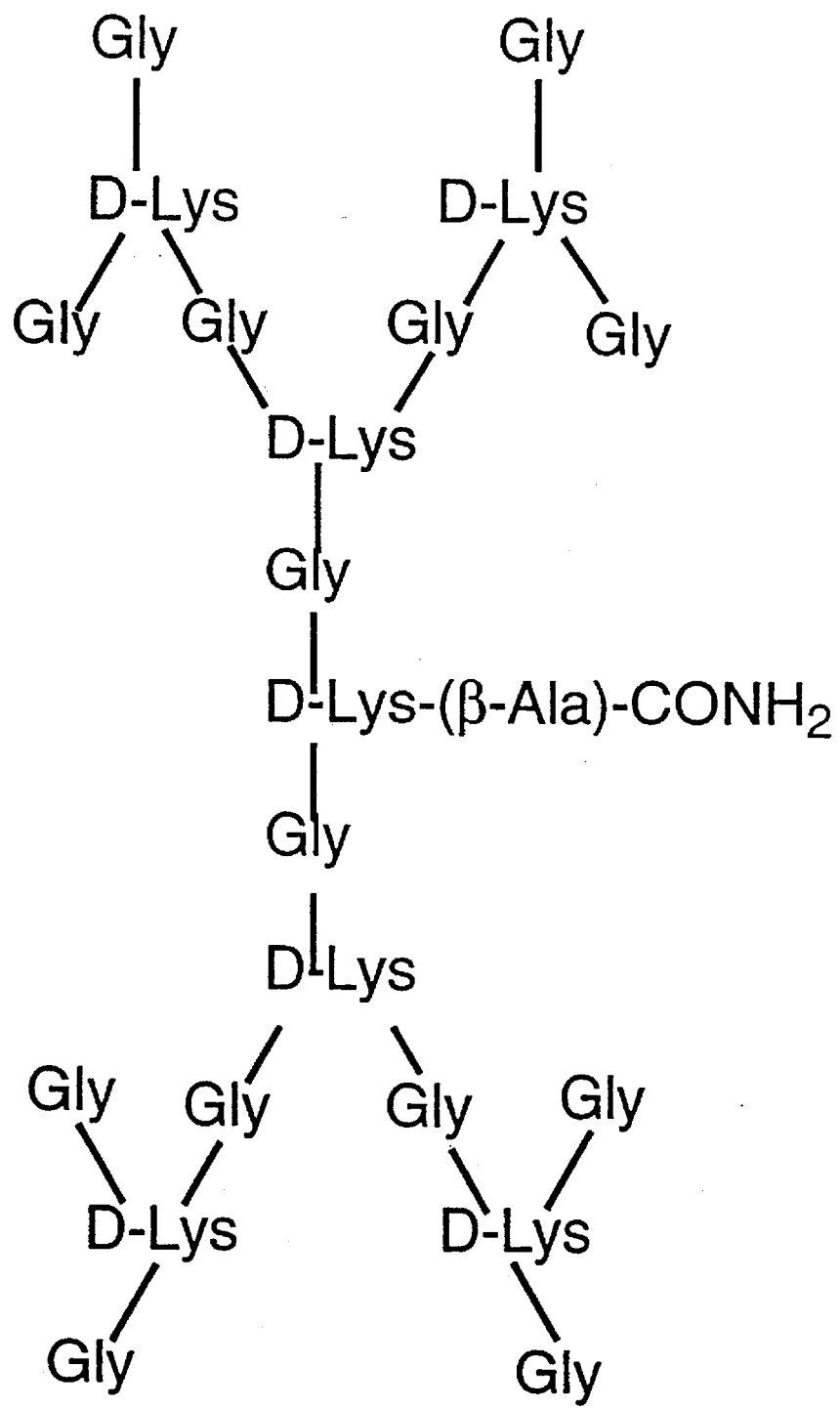
FIG. 3 illustrates the basic composition of a valence-restricted, peptide-based dendritic scaffold derived from a D-lysyl-β-alanine (amide) core peptide, subsequent glycine spacer residue addition, and two successive rounds of D-lysine, then glycine addition.

Peptide-based dendritic scaffolds, referred to herein as PBD, for peptide-based dendrimer, are derived from a core residue or core peptide that typically consists of a diamino acid(s) such as lysine (D- or L-). Each amino group of the lysine residue forms a branch point to which additional lysine residues may be added or to which a spacer amino acid such as glycine may be added followed by a lysine addition residue. The addition of each lysine residue provides a branch point for further expansion of the dendritic scaffold. With each round of lysine or spacer amino acid plus lysine addition, the number of free amino groups in the scaffold increases geometrically and can be represented by $2^x$ where x represents the number of rounds of lysine addition. For example, a scaffold synthesis based on the utilization of a D-lysyl-β-alanine (amide) core peptide, with a subsequent glycine spacer residue addition, and two successive rounds of D-lysine, followed by glycine addition, a peptide-based, dendritic scaffold may be produced which is capable of covalent modification with $2^3$, or 8 SMX moieties. That is, the potential substitution density of an SMX-specific immunosuppressive agent derived from such a dendritic scaffold, shown in FIG. 3, is equal to 8 under the conditions of this disclosure.

In this embodiment of the invention, a diamino acid other than lysine, e.g. diaminopropionic acid or diaminobutyric acid (D- or L-), may be included as the core residue or as a component of the core peptide. Homologues of glycine, e.g. ε-aminocaproic acid, may be included as alternative spacer residues. Furthermore, additional or fewer rounds of lysine (or other diamino acid) incorporation may be carried out if substitution densities greater or less than 8, respectively, are desired. All scaffolds produced in this manner are most preferably freely soluble in physiologically acceptable aqueous buffers when SMX moieties are attached.

A valence-restricted, peptide-based dendritic scaffold results in a branched or dendritic array of SMX moieties. This is in contrast to the linear array of SMX moieties that necessarily accompanies the use of a size-restricted scaffold such as dextran and the radially dispersed array of SMX moieties that necessarily accompanies the use of a valence-restricted scaffold such as β-cyclodextrin. Because an SMX-specific immunosuppressive agent derived from a valence-restricted, peptide-based dendritic scaffold is a defined molecular entity with a unique molecular weight, mass spectrometry may be employed for the purpose of confirming its structure, i.e., its SMX substitution density.

Although dendritic polymers in general represent a relatively new class of polymers, the concept of peptide-based dendritic scaffolds as carriers for a wide variety of antigens has already found application in the area of immunology. For example, this strategy has been used for preparing synthetic vaccine candidates, templates for complex immunological probes, and protein mimetics (Kaumaya et al. In Proceedings of the Twelth American Peptide Symposium. J. A. Smith and J. E. Rivier, eds. ESCOM, Leiden, 886 (1992); Stewart et al. Science: (248), 1544 (1990)). Because multiple antigens may be covalently bound to a peptide-based dendritic scaffold, any system employing this mode of antigen presentation has been referred to as a multiple antigen peptide system, or by the acronym MAPs. Further details of the MAPs technology may be found, for example, in PCT WO 90/11778 incorporated herein by reference.

Heretofore, the antigens that have been reported to be covalently arrayed using the MAPs strategy have been peptide in nature. As a result, utilization of a peptide-based, dendritic scaffold as a means of covalently arraying non-peptide SMX moieties, which are themselves antigens, represents a departure from what has appeared thus far in immunological literature pertaining to the MAPs concept. More importantly, MAPs have previously only been used in a deliberate attempt to bring on or promote an antibody response, rather than to diminish or suppress an antibody response, as is provided in the present invention.

One skilled in the art will appreciate that cyclodextrins and peptide-based dendritic molecules represent only two of several types of valence-restricted scaffolds which may be appropriate for consideration in the context of the present invention. For example, a scaffold based on repeating dipeptide units comprised of a spacer amino acid residue linked to a D-lysine residue is contemplated. This embodiment is exemplified by the following:

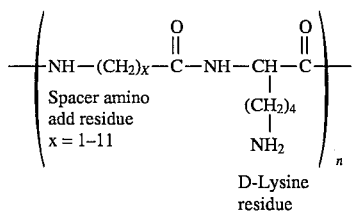

It is preferred that D-amino acid residues be incorporated into this embodiment to impart resistance to proteolytic degradation. However, L-amino acids are also contemplated. In addition, for example, a scaffold based on repeating units of hexaethylene glycol (a spacer residue) linked to a D-lysine residue may also be used according to this invention. Such a scaffold is illustrated by the following:

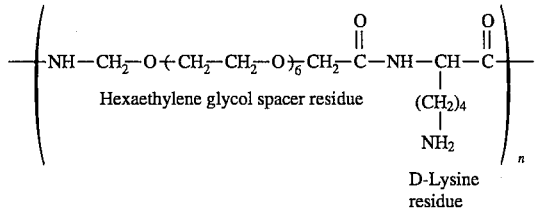

Again, it is preferred that D-amino acid residues be incorporated into this embodiment to impart resistance to proteolytic degradation, although L-amino acids are also contemplated. Valence-restricted scaffolds such as the above mentioned examples would employ the ε-amino group of the D-lysine residue as the scaffold appendage moiety, and the linking entities described above for SMX attachment purposes. These scaffolds, being valence restricted, have the advantage of being defined molecular entities.

Finally, although SMX arrayed on both size- and valence-restricted scaffolds has been found to exhibit the desired immunosuppressive properties, because polyanions may cause activation of complement, intrinsic coagulation and fibrinolytic pathways, it may be advantageous to eliminate, perhaps completely, the anionic character of the arrayed SMX moieties. (The pKa of the SMX sulfonamide moiety is 5.6.) This may be accomplished by either, i) arraying only the 3-amino-5-methyl-isoxazole portion of SMX or by, ii) arraying an N-alkylated (e.g., N-methyl) SMX derivative. In keeping with the basic description of the present invention, these anticipated changes are depicted by the following modified descriptions for Z:

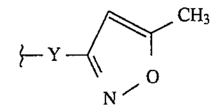

(for arrayed 3-amino-5-methyl-isoxazole)

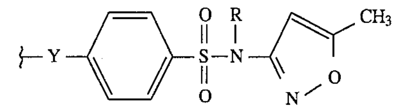

(for arrayed N-alkyl-SMX)

$R = CH_3$ (for example)

Methods and Processes of Synthesis

Dextran modified to accommodate the incorporation of SMX moieties was prepared as follows. Commercially available, size-fractionated dextran 1 of average molecular weight 40K or 70K was carboxymethylated with chloroacetic acid ($ClCH_2CO_2H$) at glucosyl C2-, C3- or C4-hydroxyl positions to yield the corresponding carboxymethyl-dextran 2. Conversion into dexamine 3 was then accomplished by reaction (of carboxymethyl-dextran) with ethylene diamine ($NH_2—CH_2—CH_2—NH_2$) in a water soluble carbodiimide (EDC=1-ethyl-3- (3-dimethylaminopropyl)carbodiimide)-mediated coupling reaction.

The presence of free amino groups in dexamine 3 allows measurement of the amine substitution density using quantitative analytical chemistry techniques (e.g., a trinitrobenzene sulfonic acid, TNBS assay (Snyder et al. Anal. Biochem.: (64), 284–288 (1975)). Expressed as the number of μmol of amine ($—NH_2$) present per milligram of dexamine 3, the value for amine density represents one expression for the theoretical maximum substitution density of SMX moieties. SMX substitution density is more conveniently expressed, however, as the number of mol of SMX bound per mol of dexamine 3, which is functionally equivalent to the number of mol of SMX bound per mol of dextran 1. Dexamine 3 used in the examples described herein was found routinely to contain approximately one primary amino group ($—NH_2$) for every five to ten glucosyl residues (or 1000–2000 g/mol) present in the dexamine 3 sample.

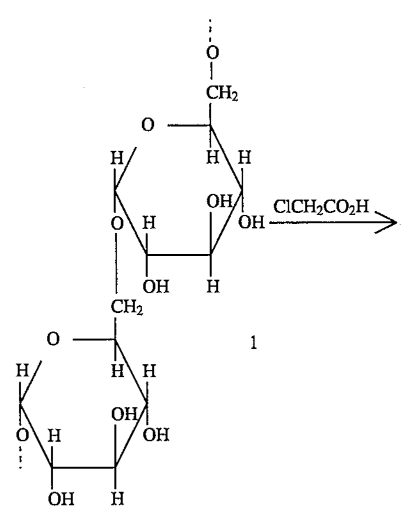

1

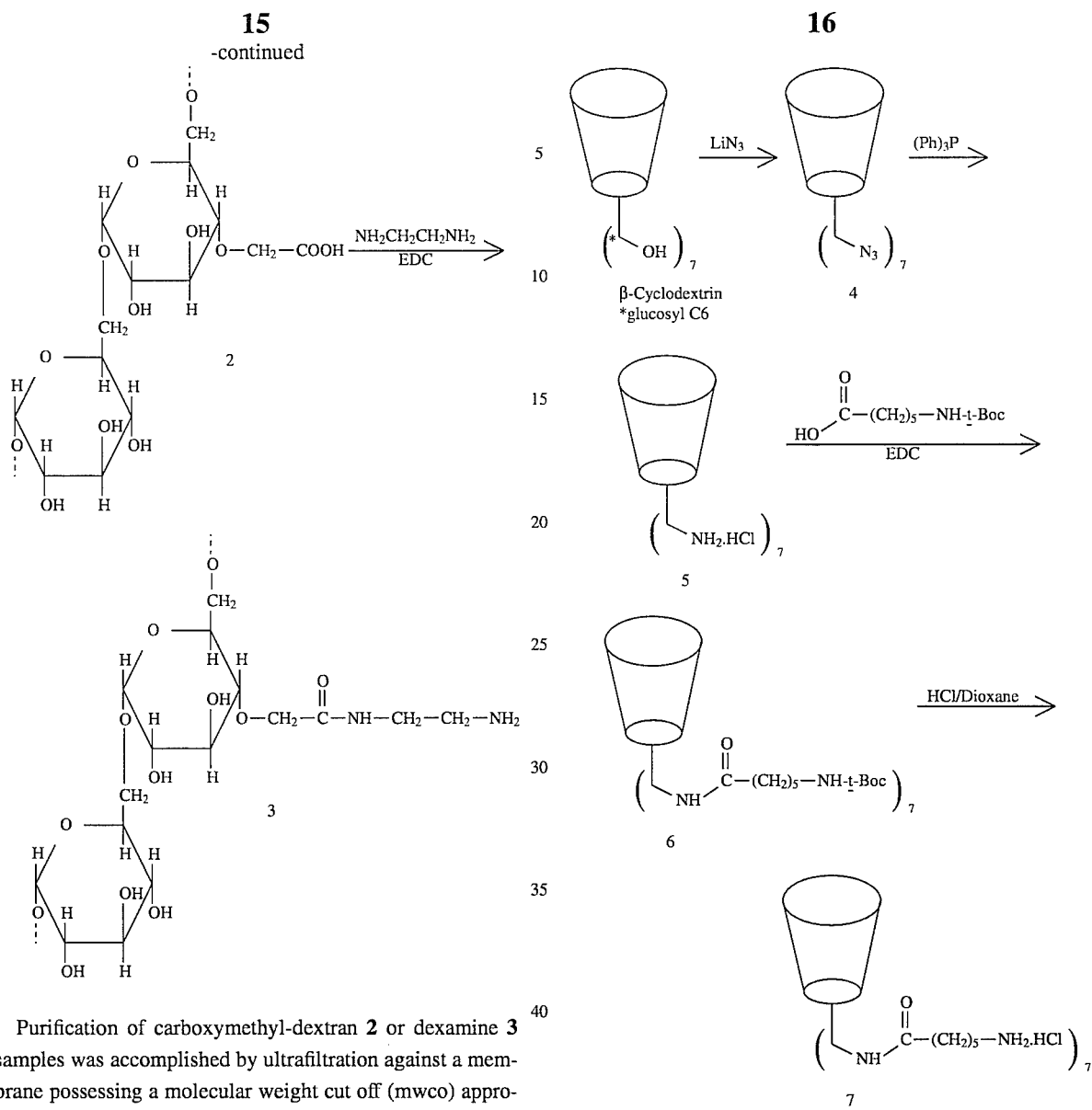

Purification of carboxymethyl-dextran 2 or dexamine 3 samples was accomplished by ultrafiltration against a membrane possessing a molecular weight cut off (mwco) appropriate for the particular dextran-based material under investigation. Molecular weight measurement of dexamine 3 samples was accomplished by laser light scattering analysis.

β-Cyclodextrin modified to accommodate the incorporation of SMX moieties was prepared as follows. Commercially available β-cyclodextrin was converted to the corresponding C6-heptaazido compound 4 with lithium azide (LiN$_3$). Reduction of 4 with triphenyl phosphine ((Ph)$_3$P) then afforded C6-heptaamino derivative 5. Coupling of 5 to N$^ε$-tert-butyloxycarbonyl-ε-aminocaproic acid was then accomplished with EDC to afford the "extended arm" product 6. Removal of the tert-butyloxycarbonyl (Boc) protecting groups with HCl/Dioxane resulted in the production of hepta-[6-(ε-aminocaproyl)amino]-β-cyclodextrin heptahydrochloride 7.

A dendritic peptide capable of accommodating the incorporation of SMX moieties was prepared by manual solid-phase peptide synthesis on a commercially available methyl benzhydryl amine (MBHA)-resin using N-tert-butyloxycarbonyl (Boc)-protected glycine (Gly), D-lysine (D-Lys) at β-alanine (β-Ala) as the protected amino acid derivatives, and dicyclohexylcarbodiimide/1-hydroxybenzotriazole (DCC/HOBt) preactivation (Barany et al., Int.J.Peptide Protein Res.: (30), 705–39 (1987)) . Stepwise addition of N-tert-butyloxycarbonyl-glycine residues to the D-lysine-generated "branch points" and cleavage from the resin resulted in the production of the branched peptide: Gly$_8$D-Lys$_4$Gly$_4$D-Lys$_2$Gly$_2$D-Lys-β-Alanine amide 14.

MBHA resin $\xrightarrow{\text{i) Boc-β-Ala} \atop \text{ii) Boc removal}}$ (β-Ala)—MBHA resin $\xrightarrow{\text{i) DiBoc-D-Lys} \atop \text{ii) Boc removal}}$

8

-continued

D-Lys—(β-Ala)—MBHA resin $\xrightarrow{\text{i) Boc-Gly} \atop \text{ii) Boc removal}}$

```
   Gly
    |
D-Lys—(β-Ala)—MBHA resin    i) DiBoc-D-Lys
    |                       ──────────────→
   Gly         10           ii) Boc removal
```

```
   D-Lys
    |
   Gly
    |
D-Lys—(β-Ala)—MBHA resin    i) Boc-Gly
    |                       ────────────→
   Gly         11           ii) Boc removal
    |
   D-Lys
   Gly\  /Gly
     D-Lys
      |
     Gly
```

```
D-Lys—(β-Ala)—MBHA resin    i) DiBoc-D-Lys
    |                       ──────────────→
   Gly                      ii) Boc removal
    /D-Lys\   12
  Gly      Gly
   |        |
 D-Lys    D-Lys
   \Gly   Gly/
      D-Lys
       |
      Gly
       |
D-Lys—(β-Ala)—MBHA resin    i) Boc-Gly
                            ii) Boc removal
                            iii) Cleavage from resin →
```

```
            13
       D-Lys
      /     \
    Gly     Gly
   /           \
 D-Lys        D-Lys
```

```
     Gly                Gly
      |                  |
    D-Lys             D-Lys
   /     \           /     \
  Gly    Gly       Gly    Gly
    \     /         \     /
      D-Lys           D-Lys
        \              /
         Gly        Gly
            \      /
         D-Lys—(β-Ala)—CONH₂
              |
             Gly
              |
            D-Lys
           /     \
         Gly    Gly      Gly   Gly
          \     /         \    /
          D-Lys           D-Lys
            \              /
             Gly        Gly
                  14
```

SMX-specific immunosuppressive agents (R-[X-Y-Z]$_n$) of Class I can be synthesized as follows. Scaffolds such as 3, 7, or 14 can be acylated with N-acetyl-L-tyrosine-N-hydroxysuccinimide ester 15 to yield the corresponding N-acetyl-L-tyrosylated scaffold 16. Sulfamethoxazole 17, diazotized with NaNO$_2$/HCl to yield aromatic diazonium salt 18, can then be coupled to the (scaffold) tyrosyl residues via an aromatic substitution reaction. The resulting azobenzene-type SMX compound 19, representative of Class I, can then be purified/isolated by ultrafiltration, size exclusion chromatography and/or C$_{18}$ reversed-phased chromatography.

SMX-specific immunosuppressive agents (R-[X-Y-Z]$_n$) of Class II can be prepared by the following method. Sulfamethoxazole 17 can be monoacylated with glutaric anhydride 20 to yield N$^4$-(4-carboxybutanoyl)-sulfamethoxazole 21. Preactivation of 21 with EDC/N-hydroxysuccinimide (NHS), to afford active ester 22, or in situ activation of 21 with EDC, and subsequent coupling to the scaffold can then be carried out to produce the desired amide bond-linked SMX compound 23. Purification/isolation of this material can be accomplished by size exclusion chromatography, ultrafiltration and/or C$_{18}$ reversed-phased chromatography.

SMX-specific immunosuppressive agents (R—[X—Y—Z]$_n$) of Class III can be prepared as follows. Scaffolds such as 3, 7, or 14 can be acylated with the heterobifunctional acylating agent: γ-maleimido-n-butyric acid N-hydroxysuccinimide ester (GMBS) to yield the corresponding γ-maleimido-n-butyryl (GMB)-scaffold 24. Michael reaction of 24 with thiol-containing sulfamethoxazole derivative 25, N$^4$-(5-cysteaminylglutaryl)-sulfamethoxazole, can then be carried out to produce the desired succinimide-based, thioether-linked SMX construct 26. Purification/isolation of this material can be accomplished by ultrafiltration, size exclusion chromatography and/or C$_{18}$ reversed-phase chromatography.

SMX-specific immunosuppressive agents (R—[X—Y—Z]$_n$) of Class IV can be synthesized as follows. γ-Bromoacetamido-n-butyric acid 27 can be converted to the heterobifunctional acylating agent: γ-bromoacetamido-n-butyric acid N-hydroxysuccinimide ester (GBBS, 28) via DCC/N-hydroxysuccinimide (NHS). Subsequent acylation of the scaffold with GBBS can be carried out to yield the corresponding γ-bromoacetamido-n-butyryl (GBB)-scaffold 29. Reaction of 29 with thiol-containing sulfamethoxazole derivative 25, N$^4$-(5-cysteaminylglutaryl)-sulfamethoxazole, can then be accomplished to afford the desired non-succinimide-based, thioether-linked SMX construct 30. Alternatively, acylation of the scaffold can be conducted with bromoacetic anhydride to yield the corresponding bromoacetylated scaffold 31. Reaction of 31 with 25 will produce a second type of non-succinimide-based, thioether linked SMX construct 32. Purification/isolation of these materials can be accomplished by ultrafiltration, size exclusion chromatography and/or C$_{18}$ reversed-phase chromatography.

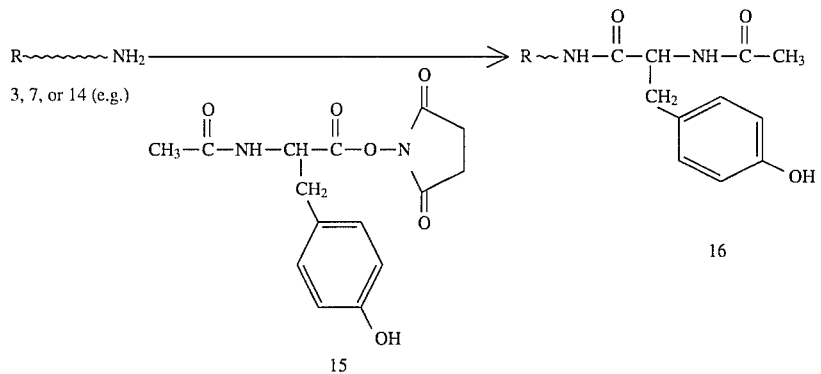
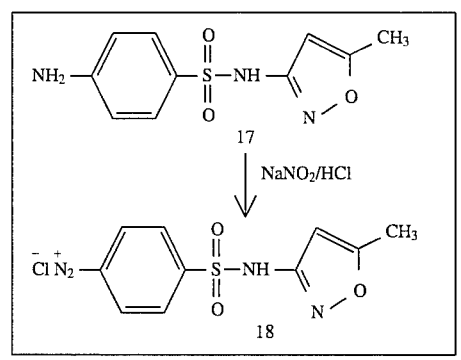
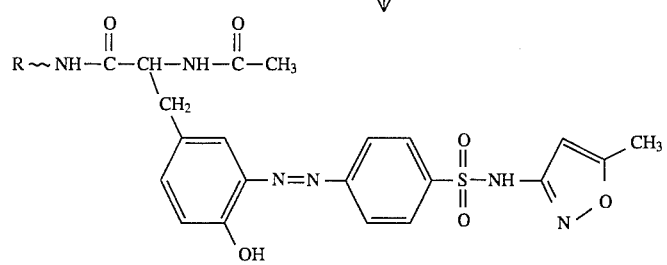
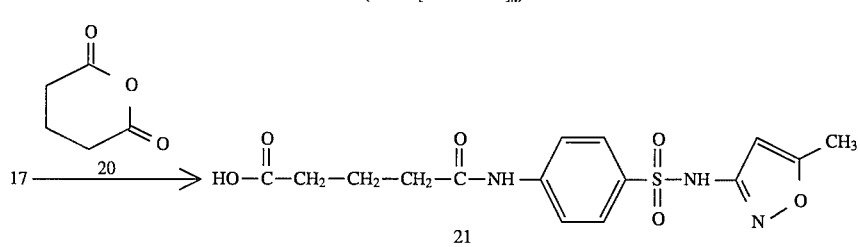
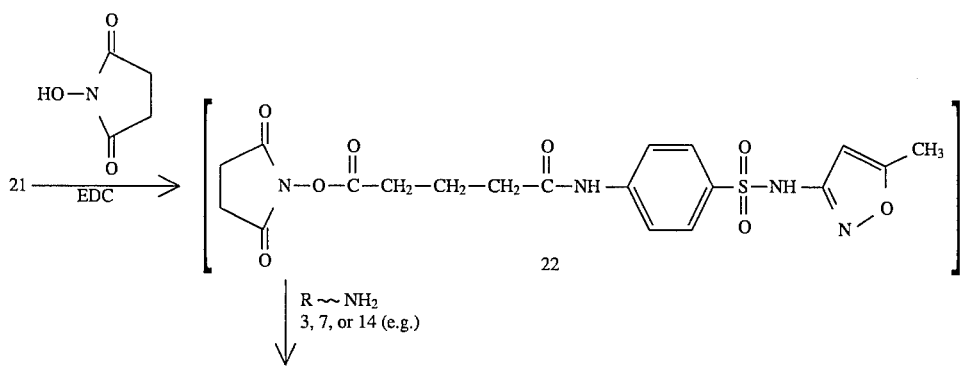

-continued
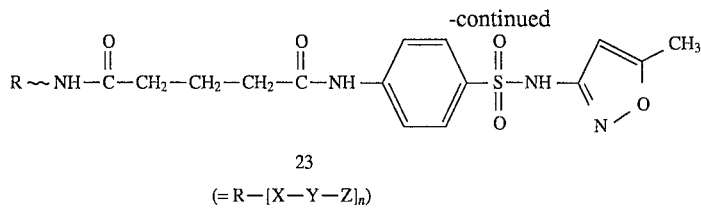
23
(= R—[X—Y—Z]$_n$)
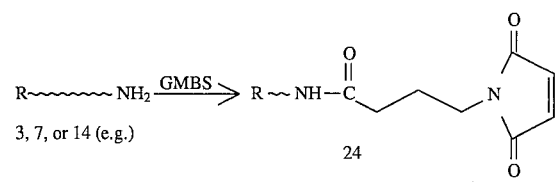
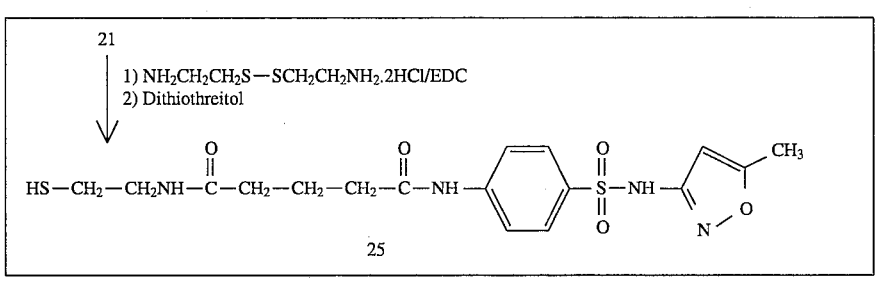
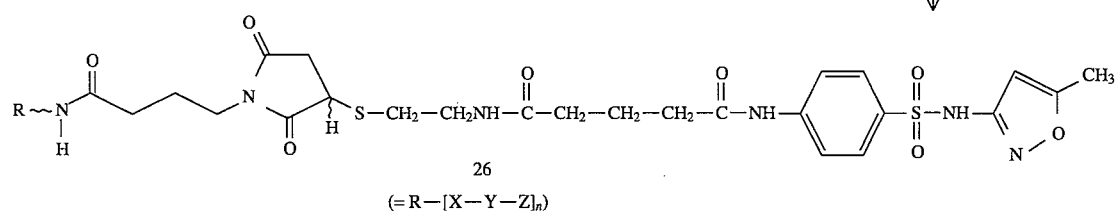
26
(= R—[X—Y—Z]$_n$)
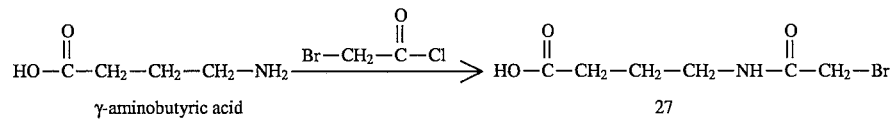
γ-aminobutyric acid
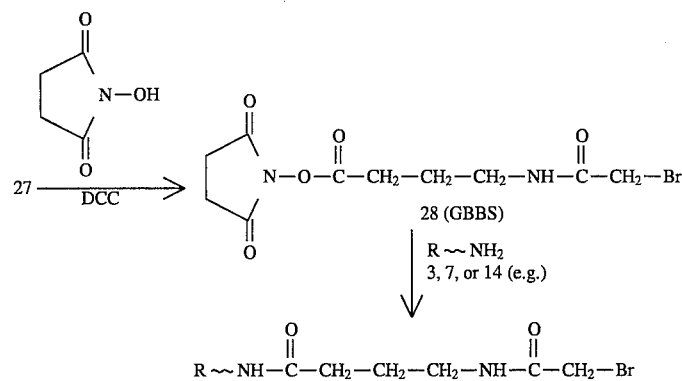
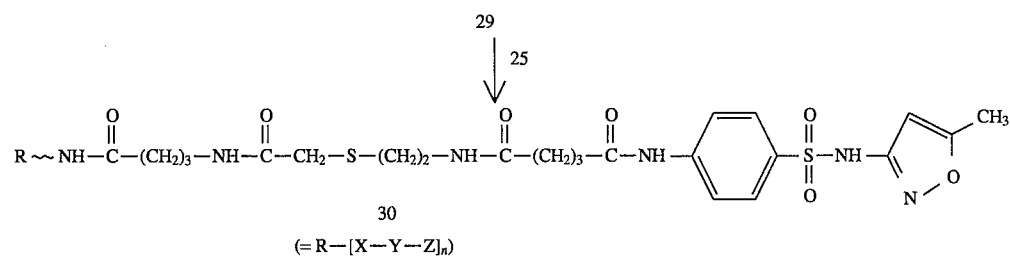
30
(= R—[X—Y—Z]$_n$)

-continued

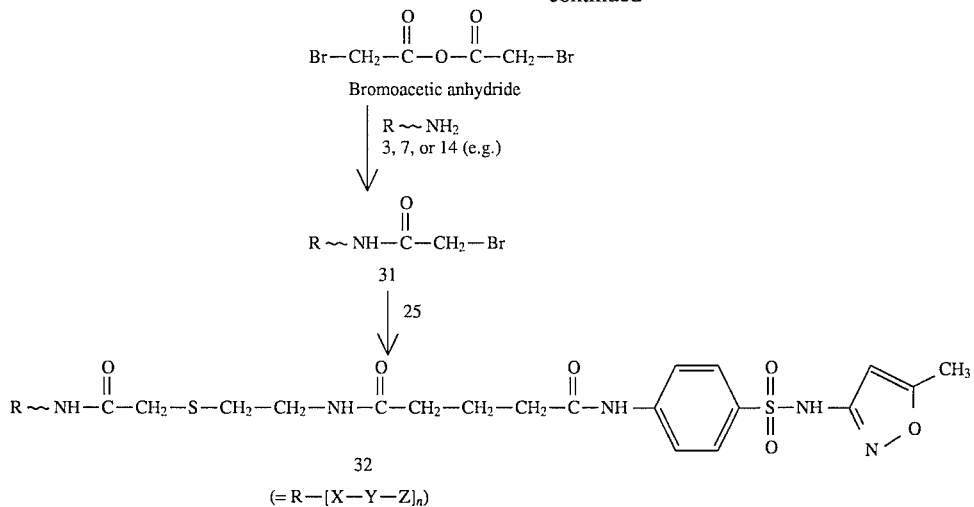

According to the present invention, pre-existing antibody responses may be selectively and specifically abrogated by treatment with the above-described SMX-scaffold constructs.

Anti-SMX antibodies were induced in mice by immunization with SMX covalently attached to keyhole limpet hemocyanin (KLH), a protein carrier, using Class I (azobenzene) linking chemistry. Mice produced IgG antibodies to both SMX and the carrier. The animals were then treated with either phosphate-buffered saline (PBS) or a suppressive SMX construct. Those animals receiving saline showed no significant change in their anti-SMX antibody levels while the mice treated with SMX construct lost their antibodies and remained suppressed for at least 60 days. At 80 days after treatment, mice were re-immunized with SMX-carrier and the number of anti-SMX antibody secreting cells in their spleens measured 3 days later. Those animals which had been SMX construct-treated had few anti-SMX antibody secreting cells in their spleens, in contrast to the PBS control mice. In another experiment, mice which had anti-SMX IgE as well as anti-SMX IgG antibodies were treated with PBS or SMX construct as before, and a similar result was obtained, that is, SMX construct-treated animals lost their anti-SMX IgE antibodies, for at least 21 days.

In addition to removal of a pre-existing antibody response, the IgG response to SMX may be prevented by prophylactic treatment with SMX constructs. Mice were treated with SMX construct the day before, the day of, or the day after immunization with an SMX-carrier protein construct. Anti-SMX IgG antibody levels were measured at various timepoints thereafter. Mice which had been treated with SMX construct failed to respond to immunization, while PBS controls made anti-SMX IgG antibodies.

SMX-specific immunosuppressive agents based on both size-restricted scaffolds, such as dextran, and valence-restricted scaffolds, such as β-cyclodextrin and peptide-based dendrimers (PBD), can prevent an antibody response to SMX. If mice are treated the day before immunization with SMX-β-cyclodextrin or SMX-PBD, they fail to make a significant IgG response while PBS-treated control mice make IgG.

The invention provides a method of preventing or treating an allergic response to SMX-containing compounds comprising treating an individual with therapeutically effective amounts of SMX-specific immunosuppressive agent. Also provided is a method of diagnosing or predicting susceptibility to allergic response in an individual to SMX comprising detecting the presence of anti-SMX antibodies.

It is another object of the present invention to provide pharmaceutical compositions containing the agents of the present invention in pharmaceutically acceptable carriers and methods for their use.

The agents of the present invention will normally be formulated for administration by injection (e.g., subcutaneously, intraperitoneally, intramuscularly, etc.) or orally. Accordingly, they will typically be combined with pharamceutically acceptable aqueous carriers such as saline, Ringer's solution, dextrose solution, and the like. The agents are administered to an individual in amounts sufficient to at least re-establish tolerance to compositions containing sulfamethoxazole. Such amounts are referred to herein as "therapeutically effective" amounts. The particular dosage regimen i.e., dose, timing and repetition, will depend upon the particular individual, and that individual's medical history, but will be generally be in the range of 2–1000 mg. Repetitive administrations may be required to achieve and/ or maintain a state of immune tolerance.

The invention will now be described further by the following working examples which are presently preferred embodiments of the invention. These examples are intended to be illustrative and instructive and are not intended to limit the scope of the instant invention.

EXAMPLES

Example 1

Dexamine$_{40K}$

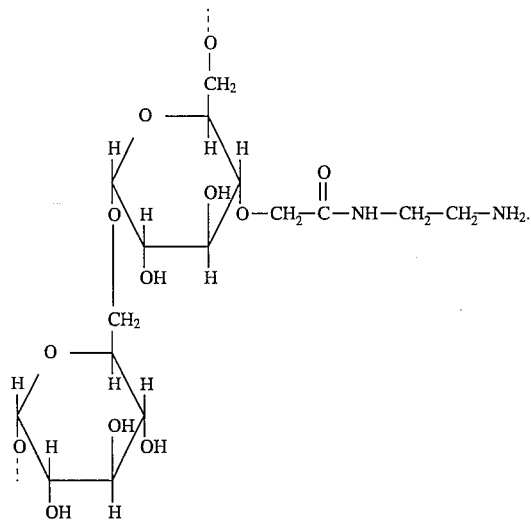

Intermediate A(1): Carboxymethyl-dextran$_{40K}$

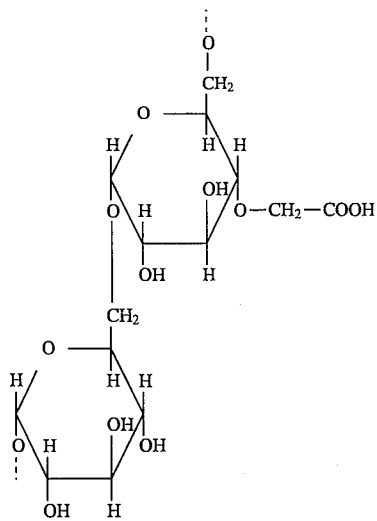

Sodium hydroxide (675 mmol, 135 mL of 5M NaOH) was added to 0.3 L of water and the resulting solution chilled in an ice-water bath (0° C.) with stirring. Chloroacetic acid (64.4 g, 685 mmol) was then added and stirring continued at 0° C. until complete dissolution occurred. The resulting solution was allowed to warm to room temperature and the pH was adjusted to ca.7 by the addition of either NaOH or chloroacetic acid. After being diluted to 0.5 L total volume, 185 mL of the chloroacetate solution was added to dextran$_{40K}$ (5.72 g, 0.143 mmol) and the carboxymethylation reaction initiated by the addition of 50 mL of 10M NaOH (500 mmol). The reaction mixture was diluted to 250 mL total volume and carboxymethylation allowed to proceed for 20 hours at 37° C. The reaction was then terminated by adjusting the solution pH to ca. 7 with 6M HCl. After being allowed to cool to room temperature, the reaction mixture was ultrafiltered against a 10,000 mwco membrane (10 volume changes of water) and the resulting carboxymethyl-dextran$_{40K}$ isolated by lyophilization.

Compound 1: Dexamine$_{40K}$

Carboxymethyl-dextran$_{40K}$ (Intermediate (A) (1), 0.143 mmol reaction scale product isolated above) was dissolved in 300 mL of water and ethylene diamine was added (45 g, 750 mmol). The resulting solution was stirred at room temperature and the pH adjusted to ca. 5 with 1M HCl. 1-Ethyl-3-(3-dimethylaminopropyl)carbodiimide (EDC, 4 g, 20.86 mmol) was then added portionwise over a 10 to 20 minute period with continuous stirring. The pH of the reaction mixture was checked every 15 minutes thereafter and maintained near 5 (via the addition of 1M HCl) for 4 hours. Ultrafiltration was carried out against a 10,000 mwco membrane (2×30% AcOH, 2×water, 2×30% AcOH, 1×1M NaCl, 3×water) and the resulting dexamine$_{40K}$ isolated by lyophilization. Yield: 4.89 g (85.4% based on no change in MW$_{avg}$).

Measurement of the amine substitution density, carried out with trinitrobenzenesulfonic acid (TNBS), yielded a value of 0.554 μmol —NH$_2$/mg for this particular preparation of dexamine$_{40K}$, a value equivalent to a theoretical maximum SMX substitution density of 22 mol of SMX per mol of Dex$_{40}$ (i.e., dextran$_{40K}$ or dexamine$_{40K}$). Laser light scattering analysis of dexamine$_{40K}$ prepared in this manner typically yielded the following molecular weight information: M$_n$ (number average molecular weight)=3.97×10$^4$ g/mol; M$_w$ (weight average molecular weight)=4.93×10$^4$ g/mol.

Example 2

Compound 2: Dexamine$_{70K}$

In a manner completely analogous to that specified above for dexamine$_{40K}$, dexamine$_{70K}$ was prepared from dextran$_{70K}$ through the intermediacy of carboxymethyl-dextran$_{70K}$. The overall yield for the two-step process was 94.6% (based on no change in MW$_{avg}$).

Measurement of the amine substitution density, carried out with trinitrobenzenesulfonic acid (TNBS), yielded a value of 0.978 μmol —NH$_2$/mg for this particular preparation of dexamine$_{70K}$, a value equivalent to a theoretical maximum SMX substitution density of 68 mol of SMX per mol of Dex$_{70}$ (i.e., dextran$_{70K}$ or dexamine$_{70K}$). Laser light scattering analysis of dexamine$_{70K}$ prepared in this manner typically yielded the following molecular weight information: M$_n$ (number average molecular weight)=5.86×10$^4$ g/mol; M$_w$ (weight average molecular weight)=7.11×10$^4$ g/mol.

Example 3

N-Acetyl-6-[4-azo-(sulfamethoxazolyl)]-L-tyrosyl-dexamine$_{70K}$

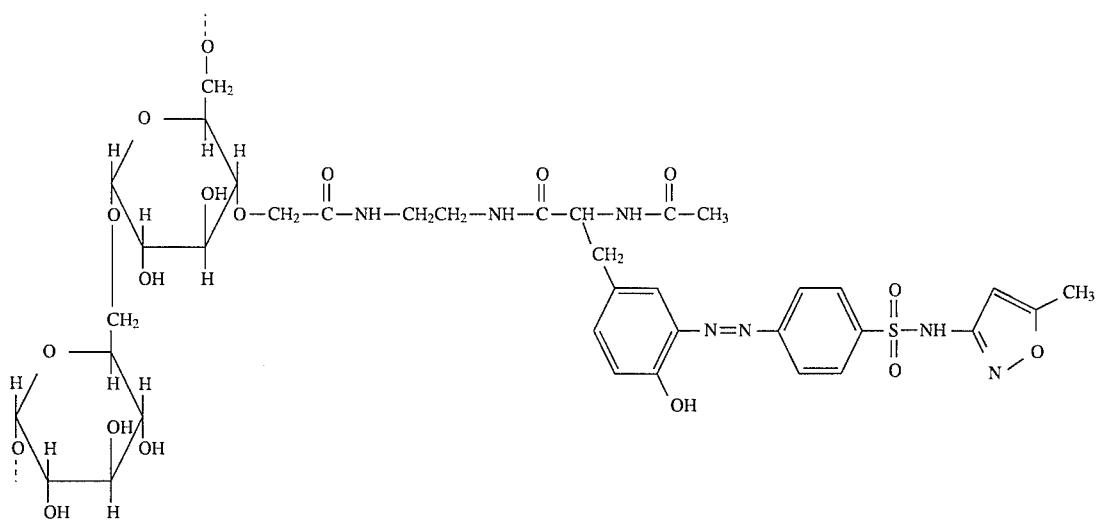

Intermediate A(3): N-Acetyl-L-tyrosine-N-hydroxysuccinimide ester

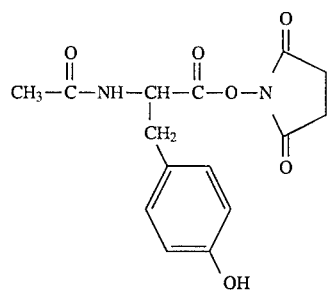

N-Acetyl-L-tyrosine (1.68 g, 7.53 mmol) was taken up in 94 mL of ethyl acetate/26 mL of acetonitrile and stirred at room temperature. N-Hydroxysuccinimide (NHS, 0.87 g, 7.56 mmol) was added and the resulting solution cooled to 0° C. under $N_2(g)$ in an ice-water bath. To the cold, stirring solution was then added dicyclohexylcarbodiimide (DCC, 1.55 g, 7.52 mmol) predissolved in 3 mL of ethyl acetate. The reaction mixture was stirred at 0° C. for 2 hours and then allowed to warm to room temperature overnight with continued stirring. The insoluble dicyclohexylurea (DCU) was removed by filtration and the resulting filtrate concentrated to a solid residue under reduced pressure. Trituration of this residue with warm ethyl acetate and subsequent storage at 4° C. then afforded a white solid. This was isolated by vacuum filtration, washed with cold ethyl acetate and dried in vacuo to yield the product in greater than theoretical yield (due to contamination with residual DCU). $^1$H-NMR (300 MHz, $CDCl_3$): δ 2.00 (s, 3H); 2.87 (s, 4H); 3.22 (m, 2H); 4.05 (m, 1H); 5.80 (d, 1H, J=7.2 Hz); 6.96 (AB quartet, 4H, J=8.4 Hz).

Intermediate B (3): N-Acetyl-L-tyrosyl-dexamine$_{70K}$

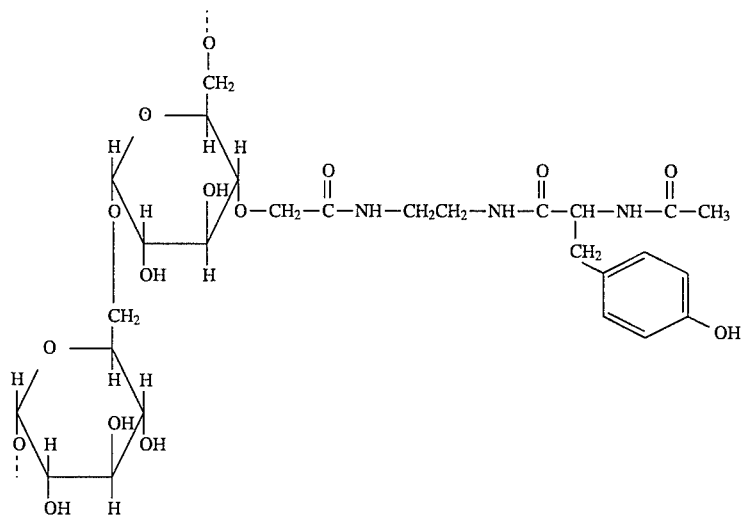

Dexamine$_{70K}$ (Compound 2, 0.238 g, 3.4 μmol, 157 μmol total amine) was dissolved in 5 mL of water and 14 mg (167 μmol) of NaHCO$_3$ was added. This solution was stirred at room temperature while N-acetyl-L-tyrosine-N-hydroxysuccinimide ester (Intermediate A(3), 0.075 g, 235 μmol), predissolved in anhydrous acetonitrile (3 mL), was added dropwise over a 2 minute period from a pressure equalizing addition funnel. The resulting reaction mixture was stirred at room temperature for 72 hours after which time it was diluted to ca. 20 mL with water and filtered to remove a small amount of insoluble material (presumably DCU). The resulting filtrate was then dialyzed with water over a 6 day period in 6000–8000 mwco dialysis tubing (SpectraPot). The final dialysate was filtered and lyophilized to afford the product as a white, fluffy solid. Yield: (0.11 g, 46%). Amino acid analysis of this material indicated the presence of ca. 15 mol of N-acetyl-L-tyrosine per mol of Dex$_{70}$. Ultraviolet spectroscopy revealed definite absorption bands at 222 nm and 274 nm, consistent with N-acetyl-L-tyrosine incorporation.

Intermediate C(3): Sulfamethoxazole diazonium chloride

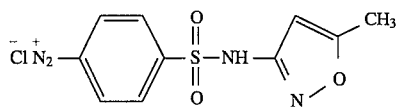

Sulfamethoxazole (30.3 mg, 120 μmol) was added to 1.6 mL of 1M HCl, stirred at room temperature for 30 minutes, and then cooled to 0° C. with stirring in an ice-water bath. A 14 mg/mL solution (=0.2 M) of NaNO$_2$/water was prepared and 1.15 mL of this solution was added dropwise to the stirring, 0° C. solution of sulfamethoxazole/1M HCl. The resulting sulfamethoxazole diazonium chloride was used immediately as described below.

Compound 3: N-Acetyl-6-[4-azo-(sulfamethoxazolyl)]-L-tyrosyl-dexamine-$_{70K}$

N-Acetyl-L-tyrosyl-dexamine$_{70K}$ (Intermediate B(3), 30 mg, 0.43 μmol, 6.4 μmol of N-acetyl-L-tyrosine equivalents) was dissolved in 10 mL of 0.13M NaCl/0.16M borate (pH 9) and cooled to 0° C. with stirring in an ice-water bath. The solution of sulfamethoxazole diazonium chloride prepared above (Intermediate C(3), containing 120 μmol of diazonium salt or approximately a 19 fold molar excess relative to the tyrosine content of the N-acetyl-L-tyrosyl-dexamine$_{70K}$ sample) was then added dropwise while maintaining the solution pH in the 9–9.5 range with 4M NaOH. Following complete addition of the diazonium salt, the reaction mixture was stirred for 1 hour at 0° C. The solution pH was then adjusted to 7.1 with concentrated HCl and the resulting preparation purified by ultrafiltration against a 10,000 mwco membrane using several volume changes of phosphate-buffered saline, then water. The final retentate was lyophilized to afford 222 mg of salt (phosphate/NaCl)-containing compound 3. Amino acid analysis of this material indicated the presence of ca. 15 mol of sulfamethoxazole-derivatized N-acetyl-L-tyrosine per mol of Dex$_{70}$ (i.e., 100% incorporation of sulfamethoxazole had been obtained).

Example 4

5-(Sulfamethoxazolyl)-glutaryl-dexamine$_{70K}$

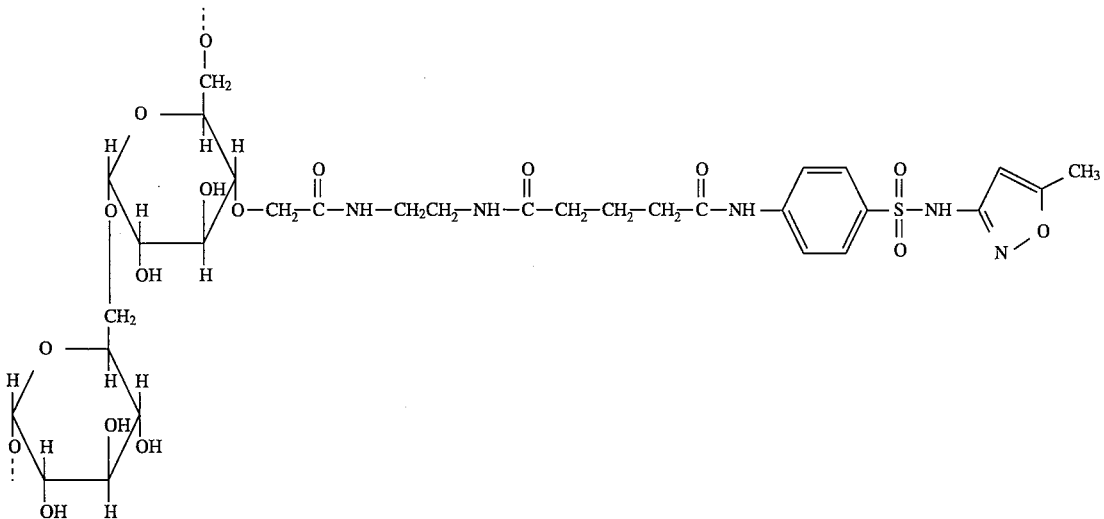

Intermediate A(4): N$^4$-(4-carboxybutanoyl)-sulfamethoxazole

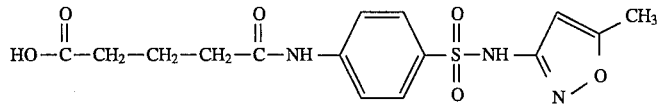

Sulfamethoxazole (5.0 g, 0.0197 mol) was dissolved in 100 mL of methylene chloride and 1 equiv of glutaric anhydride (2.25 g, 0.0197 mol) and 1 equiv of triethylamine (1.99 g, 0.0198 mol) were added. The reaction mixture was stirred at room temperature for 18 hours and then diluted with 5 volumes (500 mL) of ethyl acetate. The resulting solution was washed with 10% KHSO$_4$ (3X) and the product extracted into saturated aqueous $NaHCO_3$ (2×100 mL). The product-containing $NaHCO_3$ solution was treated with 200 mL of methylene chloride and acidified to pH 4.5 with concentrated HCl. During the acidification process, a precipitate formed that was isolated by vacuum filtration. The methylene chloride was then drawn off from the filtrate and the resulting aqueous solution washed with an additional 100 mL of methylene chloride. The final aqueous phase was acidified to pH 1 with concentrated HCl in the presence of 200 mL of ethyl acetate. The resulting ethyl acetate phase was dried over $Na_2SO_4$, filtered, and concentrated under reduced pressure to yield a white, solid residue. This was combined with the initially-isolated precipitate and the resulting (combined) solids triturated with methylene chloride. Extensive drying in vacuo afforded 6.12 g of product (0.0167 mol, 85%). $^1$-HNMR (300 MHz, $CDCl_3/DMSO$-$d_6$): δ 2.02 (p, 2H, j=7.2 Hz); 2.32 (s, 3H); 2.40 (t, 2H, J=7.1 Hz); 2.48 (t, 2H, J=7.2 Hz); 6.08 (s, 1H); 7.79 (AB quartet, 4H, J=8.85 Hz); 9.69 (br s, 1H); 9.82 (br s, 1H).
FAB Mass Spectrum:

Calculated MW=367

Found MW=368 (M+H)

Intermediate B(4): $N^4$-(4-carboxybutanoyl)-sulfamethoxazole-N-hydroxysuccinimide ester

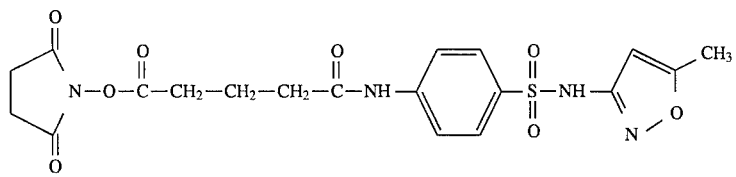

$N^4$-(4-Carboxybutanoyl)-sulfamethoxazole(Intermediate A(4), 0.08 g, 218 μmol) was dissolved in 1 mL of dimethylformamide and stirred at room temperature. N-Hydroxysuccinimide (NHS, 0.05 g, 435 μmol) was added and the resulting solution cooled to 0° C. under $N_2$ (g) in an ice-water bath. To the cold, stirring solution was added EDC (0.046 g, 240 μmol) and the reaction mixture then stirred at 0° C. for 1 hour. The resulting $N^4$-(4-carboxybutanoyl)-sulfamethoxazole-N-hydroxysuccinimide ester was used immediately as described below.

Compound 4: 5-(Sulfamethoxazolyl)-glutaryl-dexamine$_{70K}$

Dexamine$_{70K}$ (Compound 2, 50 mg, 0.71 μmol, 43.5 μmol total amine) was dissolved in 6 mL of 0.2M HEPES (pH 7.5) and stirred at room temperature. The solution of $N^4$-(4-carboxybutanoyl)-sulfamethoxazole-N-hydroxysuccinimide ester prepared above (Intermediate B(4), containing 218 μmol of active ester or approximately a 5 fold molar excess relative to the amine content of the dexamine$_{70K}$ sample) was added and stirring continued for 18 hours at room temperature. The crude reaction mixture was then applied to a 2.5×40 cm Sephadex G-25 column and the column eluted with water (flow rate=3 mL/minute). The product was collected in the void volume of the column and lyophilized to afford 50 mg of compound 4 (85%) as a white, fluffy solid. Size exclusion HPLC analysis (TSK 5000 column) revealed the product to be free of contamination from unreacted $N^4$-(4-carboxybutanoyl)-sulfamethoxazole-N-hydroxysuccinimide ester, EDC and N-hydroxysuccinimide. Spectrophotometric analysis (254 nm) indicated the presence of ca. 35 mol of sulfamethoxazole per mol of Dex$_{70}$.

Example 5

γ-[3'-(5-sulfamethoxazolylglutaramidoethylthio)]-succinimido-n-butyryl-dexamine$_{70K}$

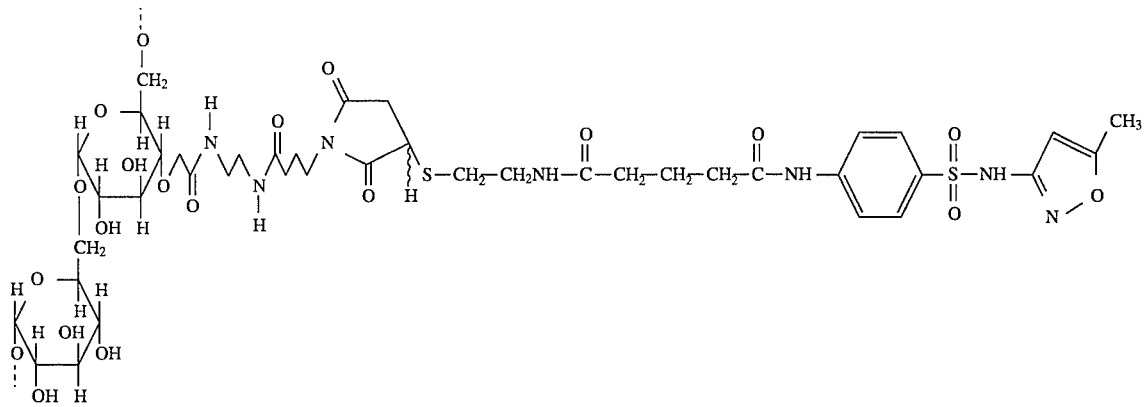

Intermediate A(5): γ-Maleimido-n-butyryl (GMB)-dexamine$_{70K}$

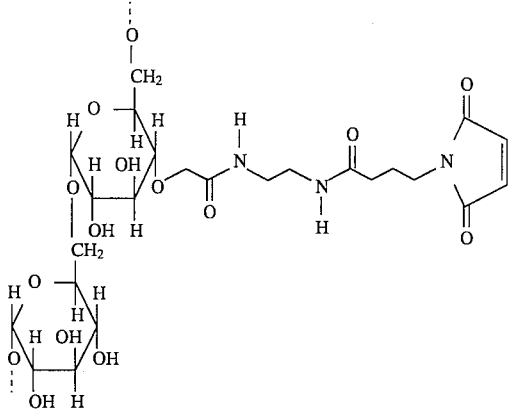

Dexamine$_{70K}$ (Compound 2, 100 mg, 1.43 μmol, 87 μmol total amine) was dissolved in 15 mL of HEPES buffer (0.2 M, pH 7.5) and stirred gently at room temperature. To the stirring solution was added γ-maleimido-n-butryic acid N-hydroxysuccinimide ester (GMBS, mg, 436 μmol or approximately a 5 fold molar excess relative to the total amine content of the dexamine$_{70K}$ sample) predissolved in 5 mL of tetrahydrofuran. The reaction mixture was stirred for 1 hour at room temperature and the product purified/isolated by ultrafiltration against a 10,000 mwco membrane using several volume changes of endotoxin-free water. Size exclusion HPLC analysis (TSK 5000 column) of the final retentate indicated the product contained therein to be free of contamination from excess GMBS, NHS and γ-maleimido n-butyric acid. Furthermore, analysis for residual free amine (—NH$_2$) with either ninhydrin or trinitrobenzenesulfonic acid indicated that complete acylation of the (dex)amino groups had been achieved. If the g-maleimido n-butyryl (GMB)-dexamine$_{70K}$ produced as described above was not to be used immediately, it was stored at 4° C. for no more than 48 hours.

Intermediate B(5): N$^4$-(5-cysteaminylglutaryl)-sulfamethoxazole

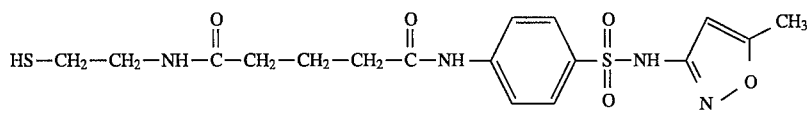

N$^{4-}$ (4-Carboxybutanoyl)-sulfamethoxazole (Intermediate A(4), 5.0 g, 0.0136 mol) was dissolved in 100 mL of dimethylformamide and 0.5 equiv of cystamine dihydrochloride (1.53 g, 0.0068 mol), 1.5 equiv of triethylamine (2.07 g, 0.0205 mol) and 2 equiv of EDC (5.2 g, 0.027 mol) were added. The reaction mixture was stirred at room temperature for 18 hours and then diluted with aqueous NaHCO$_3$ to yield a pH 8 solution. The crude disulfide contained therein was then reduced upon treatment with 2 equiv of dithiothreitol (4.0 g, 0.0272 mol) and the resulting free thiolcontaining product purified by preparative reversed-phase HPLC on a Waters Delta-Prep 3000 preparative chromatography system (47 mm x.30 cm radial compression cartridge; 300Å 15 mm C$_{18}$; 0%14 80% linear acetonitrile gradient containing 0.1% trifluoroacetic acid; 40 minutes; 100 mL/minute). Column fractions containing the product were combined, concentrated under reduced pressure and lyophilized to afford 4.0 g (0.0094 mol, 69%) of product as a white, fluffy solid. $^1$H-NMR (300 MHz, CDCl$_3$/DMSO-d$_6$): δ 1.54 (t, 1H, J=8.5 Hz); 2.03 (p, 2H, J=7.2 Hz); 2.31–2.33 (m, 5H); 2.46 (t, 2H, J=8.0 Hz); 2.66 (q, 2H, J=7.0 Hz); 3.40 (q, 2H, J=6.9 Hz); 6.08 (s, 1H); 7.39 (br s, 1H); 7.79 (AB quartet, 4H, J=8.8 Hz); 9.94 (br s, 1H); 10.91 (br s, 1H).

FAB Mass Spectrum:
Calculated MW=426
Found MW=427 (M+H)

Compound 5: γ-[3'-(5-sulfamethoxazolylglutaramidoethylthio)]-succinimido-n-butyryl-dexamine$_{70K}$ GMB-Dexamine$_{70K}$ (Intermediate A(5), ca. 1.43 μmol, ca. 87 μmol total maleimide content) was dissolved in 20 mL of HEPES buffer (0.2M, pH 7.5) to afford a 5 mg/mL solution (approx. concentration) which was stirred at room temperature. To the stirring solution was added N$^4$-(5-cysteaminylglutaryl)sulfamethoxazole (Intermediate B(5), 0.055 g, 129 μmol or approximately a 1.5 fold molar excess relative to the total maleimide content of the GMB-dexamine$_{70K}$ sample) predissolved in 3 mL of tetrahydrofuran. The reaction mixture was stirred for 2 hours at room temperature and then residual maleimide groups were quenched (or neutralized) by the addition of β-mercaptoethanol (0.068 g, 870 μmol or approximately a 10 fold molar excess relative to the total maleimide content of the GMB-dexamine$_{70K}$ sample). After stirring an additional 4 hours, the product was purified/isolated by ultrafiltration against a 10,000 mwco membrane using several volume changes of phosphate-buffered saline, then endotoxin-free water. Size exclusion HPLC analysis (TSK 5000 column) of the final retentate indicated the product contained therein to be free of contamination from excess N$^4$-(5-cysteaminylglutaryl)-sulfamethoxazole and β-mercaptoethanol. Lyophilization then afforded 68 mg (50% based on actual dexamine$_{70K}$ recovery) of compound 5 as a white, fluffy solid. Amino acid analysis of this material indicated the presence of ca. 44 mol of sulfamethoxazole per mol of Dex$_{70}$. A subsequent preparation afforded this material in 55% yield (based on actual dexamine$_{70K}$ recovery) with a substitution density of ca. 62 mol of sulfamethoxazole per mol of Dex$_{70}$.

Example 6

γ-[3'-(5-sulfamethoxazolylglutaramidoethylthio)]-succinimido-n-butyryl-dexamine$_{40K}$ In a manner completely analagous to that specified above for γ-[3'-(5-sulfamethoxazolylglutaramidoethylthio)]-succinimido-n-butyryl-dexamine$_{70K}$, γ-[3'- (5-sulfamethoxyazolylglutaramidoethylthio)]-succinimido-n-butyryl-dexamine$_{40K}$ was prepared from GMB-dexamine$_{40K}$ and N$^4$-(5-cysteaminylglutaryl)-sulfamethoxazole (Intermediate B(5)). The overall yield for the process based on dexamine$_{40K}$ as the limiting reagent was 42% (preparation 1), 67% (preparation 2), and 56% (preparation 3). Amino acid analysis of these materials indicated the presence of ca. 14 mol of sulfamethoxazole per mol of Dex$_{40}$ (preparation 1), 7 mol of sulfamethoxazole per mol of Dex$_{40}$ (preparation 2), and 22 mol of sulfamethoxazole per mol of Dex$_{40}$ (preparation 3).

Example 7

γ-[3-(5-sulfamethoxazolylglutazamidoethylthio)]-acetamido-n-butyryl-dexamine$_{40K}$

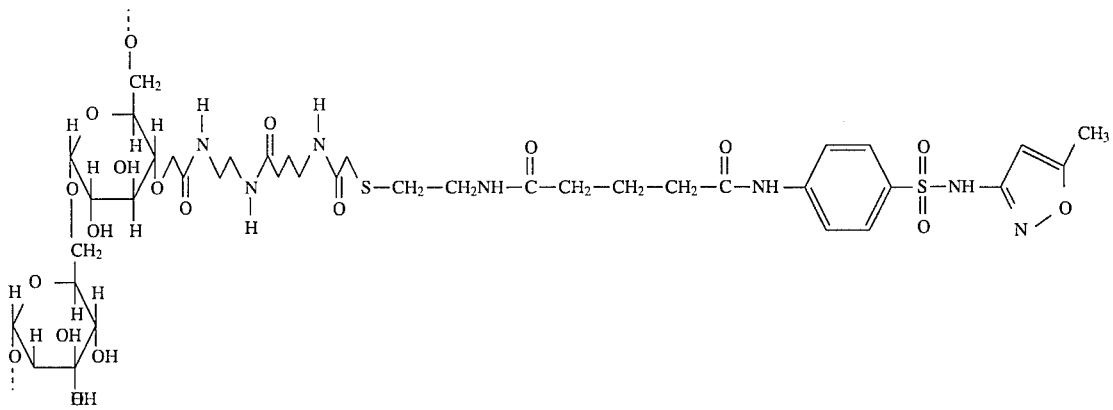

Intermediate A(7): γ-Bromoacetamido-n-butyric acid

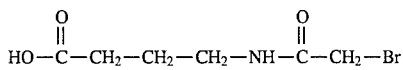

γ-Aminobutyric acid (2.0 g, 0.0194 mol) was dissolved in 100 mL of acetonitrile/water (1:1, v/v) and stirred at room temperature. To the stirring solution was added 2 equiv of triethylamine (3.92 g, 0.0387 mol) and 0.94 equiv of bromoacetyl chloride (2.86 g, 0.0182 mol). The reaction mixture was stirred for 2 hours at room temperature after which time it was diluted with 200 mL of ethyl acetate and then washed with 0.1M HCl (3×50 mL). The HCl washes were combined and re-extracted with 10% n-butanol in ethyl acetate (4X). The combined ethyl acetate was concetrated to an oil under reduced pressure. This was taken up in 50 ml of methylene chloride and then treated with 200 mL of hexanes. Brief concentration of the resulting solution under reduced pressure resulted in the formation of an oil which was triturated with hexanes to yield an oily solid. Extensive drying in vacuo afforded 1.6 g of product (0.0071 mol, 40% based on bromoacetyl chloride as the limiting reagent). $^1$H-NMR (300 MHz, CDCl$_3$): δ 1.92 (m, 2H); 2.47 (t, 3H, J =7 Hz); 3.4 (m, 2H); 3.93 (s, 2H); 6.85 (br s, 1H).

Intermediate B(7): γ-Bromoacetamido-n-butyric acid N-hydroxysuccinimide ester (GBBS)

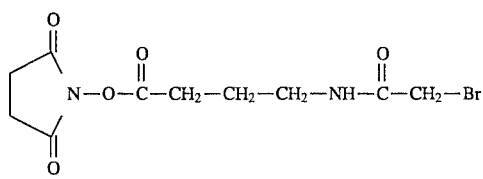

γ-Bromoacetamido n-butyric acid (Intermediate A(7), 1.0 g, 4.46 mmol) was dissolved in 89 mL of ethyl acetate/25 ml of acetonitrile and stirred at room temperature. N-Hydroxysuccinimide (NHS), 0.513 g, 4.46 mmol was added and the resulting solution cooled to 0° C. in an ice-water bath. To the cold, stirring solution was added dicyclohexylcarbodiimide (DCC, 1.013 g, 4.91 mmol). The reaction mixture was stirred at 0° C. for 1 hour and then allowed to warm to room temperature overnight with continued stirring. The insoluble dicyclohexylurea (DCU) was removed by filtration and the resulting filtrate concentrated to an oily residue under reduced pressure. Treatment with hot 2-propanol and subsequent storage at −10° C. afforded the product as a white solid. This was isolated by vacuum filtration and dried in vacuo to yield 1.26 g (3.92 mmol, 88%) of product. $^1$H-NMR (300 MHz, CDCl$_3$): δ 2.04 (p, 2H, J=7 Hz); 2.70 (t, 2H, J=7 Hz); 2.87 (br s, 4H); 3.44 (q, 2H, J=6.6 Hz); 3.89 (s, 2H); 6.78 (br s, 1H).

Intermediate C(7): γ-Bromoacetamido-n-butyryl (GBB)-dexamine$_{40K}$

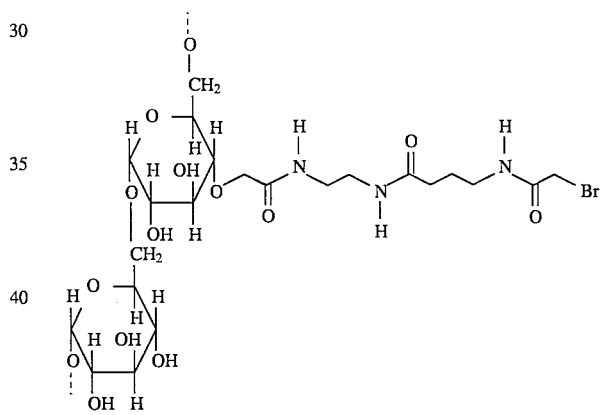

Dexamine$_{40K}$ (Compound 1, 100 mg, 2.5 μmol, 55.4 μmol total amine) was dissolved in 8 mL of HEPES buffer (0.2M, pH 7.5) and stirred gently at room temperature. To the stirring solution was added γ-bromoacetamido-n-butyric acid N-hydroxysuccinimide ester (GBBS, Intermediate B(7), 88.9 mg, 277 μmol or approximately a 5 fold molar excess relative to the total amine content of the dexamine$_{40K}$ sample) predissolved in 0.4 mL of tetrahydrofuran. The reaction mixture was stirred for 2.5 hours at room temperature and the product then purified/isolated by ultrafiltration against a 10,000 mwco membrane using several volume changes of endotoxin-free water. Size exclusion HPLC analysis (TSK 5000 column) of the final retentate indicated the product contained therein to be free of contamination from excess GBBS, NHS and γ-bromoacetamido-n-butyric acid. The γ-bromoacetamido-n-butyryl (GBB)-dexamine$_{40K}$ produced in this manner was used immediately as described below.

Compound 7: γ- [3- (5-sulfamethoxazolylglutaramidoethylthio)]-acetamido-n-butyryl-dexamine$_{40K}$ GBB-Dexamine$_{40K}$ (Intermediate C(7), ca. 2.5 μmol, ca. 55.4 mol total bromoacetamide content) was dissolved in 10 mL of phosphate-buffered saline (0.01M phosphate, 0.15M sodium chloride; pH 7) that contained 70.8 mg (166 μmol or approximately a 3 fold molar excess relative to the total bromoacetamide content of the GBB-Dexamine$_{40K}$ sample) of dissolved N4-(5-cysteaminylglutaryl)-sulfamethoxazole (Intermediate B(5)). The resulting pH 7.8 reaction mixture was stirred for 16 hours at room temperature and then residual bromoacetamide groups were quenched (or neutralized) by the addition of β-mercaptoethanol (0.043 g, 550 μmol or approximately a 10 fold molar excess relative to the total bromoacetamide content of the GBB-Dexamine$_{40K}$ sample). After stirring an additional 5 hours, the product was purified/isolated by ultrafiltration against a 10,000 mwco membrane using several volume changes of endotoxin-free water. Size exclusion HPLC analysis (TSK 5000 column) of the final retentate indicated the product contained therein to be free of contamination from excess $N^4$-(5-cysteaminylglutaryl)-sulfamethoxazole and β-mercaptoethanol. Lyophilization then afforded 93 mg (81% based on actual dexamine$_{40K}$ recovery) of compound 7 as a white, fluffy solid. Amino acid analysis of this material indicated the presence of ca. 13.8 mol of sulfamethoxazole per mol of Dex$_{40}$.

Example 8

Hepta-[6-(ε-aminocaproyl)amino]-β-cyclodextrin heptahydrochloride

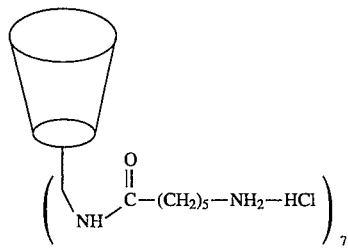

Intermediate A(8): Hepta-[6-azido]-β-cyclodextrin

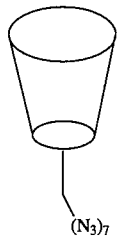

To a stirring solution of β-cyclodextrin (20.12 g, 17.73 mmol) in 350 mL of dimethylformamide at 0° C. was added lithium azide (LiN$_3$, 34.72 g, 709 mmol) and triphenyl phosphine ((Ph)$_3$P, 65.11 g, 248 mmol). A solution of carbon tetrabromide (CBr$_4$, 82.32 g, 248 mmol) in dimethylformamide (125 mL) was then added dropwise via a pressure equalizing addition funnel while the temperature of the stirring reaction mixture was maintained at 0° C. Following complete addition of the CBr$_4$/dimethylformamide solution, the reaction mixture was allowed to warm to room temperature and stirring was then continued for 48 hours at which time the reaction was quenched (overnight) by the addition of 100 mL of methanol. The reaction mixture was then concentrated under reduced pressure and the resulting concentrate added to a large volume excess of water with development of a semi-solid residue. After decanting the excess water, the residue was triturated with methanol to afford a white solid. This was isolated by vacuum filtration, washed well with benzene and dried in vacuo to yield 19.46 g (14.70 mmol, 83%) of product. $^1$H-NMR (300 MHz, DMSO-d$_6$): δ 3.40–4.15 (m, 49H); 5.08 (br s, 7H); 5.93 (s, 7H); 6.10 (d, 7H).

Intermediate B(8): Hepta-[6-amino]-β-cyclodextrin heptahydrochloride

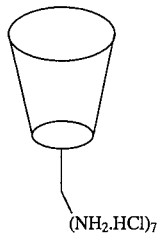

To a stirring solution of hepta-[6-azido]-β-cyclodextrin (Intermediate A(8), 21.32 g, 16.10 mmol) in 300 mL of dioxane at room temperature was added triphenylphosphine ((Ph$_3$)P, 88.70 g, 338 mmol) and 60 mL of methanol. The reaction mixture was stirred for 1.5 hours at which time 30% ammonium hydroxide was added (15.03 mL, 129 mmol) and stirring continued for an additional 24 hours. The quenched reaction mixture was then concentrated under reduced pressure and the resulting concentrate treated with a large volume excess of water. The heterogenous mixture that developed was acidified by the addition of 1M HCl, stirred vigorously and filtered to remove a white precipitate (primarily (Ph)$_3$P=O). The aqueous filtrate was washed with benzene (3X) and then concentrated under reduced pressure to afford 7.51 g (5.37 mmol, 33%) of product. An additional 7.05 g (5.04 mmol, 31%) of product was obtained by stirring the initally isolated white precipitate in water overnight and concentrating the resulting aqueous filtrate. Total yield: 14.56 g (10.42 mmol, 65%). This material was used without further purification as described below.

Intermediate C(8): Hepta-[6-(N$^ε$-tert-butyloxycarbonyl-ε-aminocaproyl)amino]-β-cyclodextrin

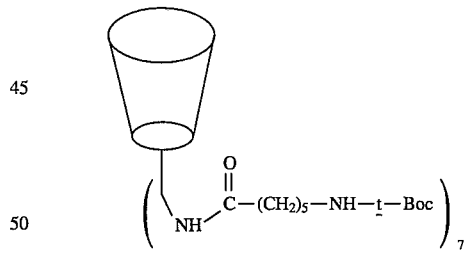

Hepta-[6-amino]-β-cyclodextrin heptahydrochloride (Intermediate B(8), 14.56 g, 10.42 mmol) was dissolved in 300 mL of dimethylformamide and stirred at room temperature. To the stirring solution was then added successively N-methylmorpholine (8.42 g, 83.2 mmol) N$^ε$-tert-butyloxycarbonyl-ε-aminocaproic acid (21.62 g, 93.6 mmol) and EDC (17.94 g, 93.6 mmol). The resulting reaction mixture was stirred at room temperature for 6 days at which time it was diluted with water and extracted with ethyl acetate (3X). The combined ethyl acetate layers were washed succesively with 1M HCl and saturated sodium chloride (1X each), then dried over sodium sulfate and concentrated under reduced pressure to afford 20.29 g (7.70 mmol, 74%) of product as a pale, 5 yellow oil. The $^1$H-NMR spectrum (300 MHz, DMSO-d$_6$) of this material indicated the presence of tert-butyloxycarbonyl (group) resonances at δ 1.35. This material was used without further purification as described below.

Compound 8: Hepta-[6-(ε-aminocaproyl)amino]-β-cyclodextrin heptahydrochloride

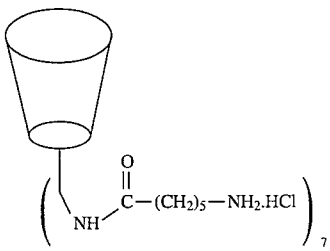

Hepta- [6-(N^ε-tert-butyloxycarbonyl-ε-aminocaproyl) amino]-β-cyclodextrin (Intermediate C(8), 20.29 g, 7.70 mmol) was treated with 60 mL of HCl-saturated dioxane (4N) and stirred at room temperature overnight. The reaction mixture was then filtered and the resulting (collected) white solid washed well with dioxane and dried in vacuo to afford 12.0 g (5.53 mmol, 72%) of compound 8. The $^1$H-NMR spectrum (300 MHz, DMSO-$d_6$) of this material indicated that complete deprotection, i.e., removal of the tert-butyloxycarbonyl groups, had been achieved. This material was used without further purification as described below.

Example 9

Hepta-[6-(5-sulfamethoxazolylglutaryl-ε-aminocaproyl) amino]-β-cyclodextrin to the total amine content of the β-cyclodextrin sample). The resulting reaction mixture was then cooled to 0° C. in an ice-water bath and treated with EDC (0.20 g, 1.04 mmol or approximately a 3.2 fold molar excess relative to the total amine content of the β-cyclodextrin sample) and catalytic dimethylamino pyridine (DMAP, ca. 5 mg, ca. 0.041 mmol or ca. 13 mol%). Stirring was continued for 1 hour at 0° C. and then overnight at room temperature. The reaction mixture was diluted into 100 mL of ethyl acetate, treated with 50 mL of 0.1M HCl, and stirred vigorously at which time an oily solid separated from solution. This was purified by preparative reversed-phase HPLC on a Waters Delta-Prep 3000 preparative chromatography system (47 mm×30 cm radial compression cartridge; 300Å 15 μm $C_{18}$; 0%–80% linear acetonitrile gradient containing 0.1% trifluoroacetic acid; 40 minutes; 100 mL/minute). Column fractions containing the product were combined, concentrated under reduced pressure and lyophilized to afford 24 mg (0.0055 mmol, 12%) of compound 9 as a white powder.

Low Resolution Laser Desorption Mass Spectrum

Calculated MW+Na=4399

Found MW=4401 (within known 0.1% MW experimental error of instrumentation.)

Amino acid analysis of this material confirmed the presence of 7 mol of sulfamethoxazole per mol of β-cyclodextrin.

Example 10

Hepta-[6-(γ-3'-(5-sulfamethoxazolylglutaramidoethylthio)-succinimido-n-butyryl-ε-aminocaproyl)amino]-β-cyclodextrin

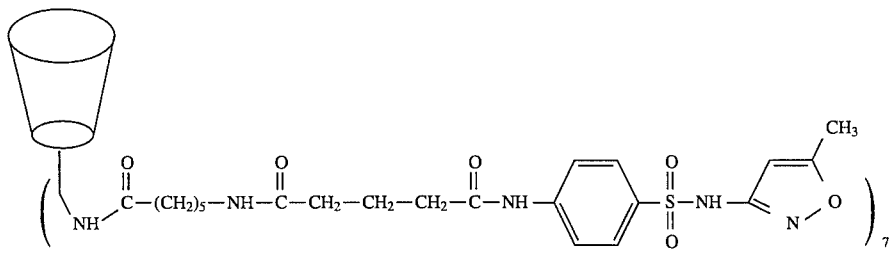

Hepta- [6-(ε-aminocaproyl)amino]-β-cyclodextrin heptahydrochloride (Compound 8), 100 mg, 0.046 mmol) was dissolved in 10 mL of dimethylformamide and stirred at room temperature. To the stirring solution was added successively triethylamine (0.049 g, 0.48 mmol), water (1 mL, to enhance dissolution of the reactants) and N^4-(4-carbox-

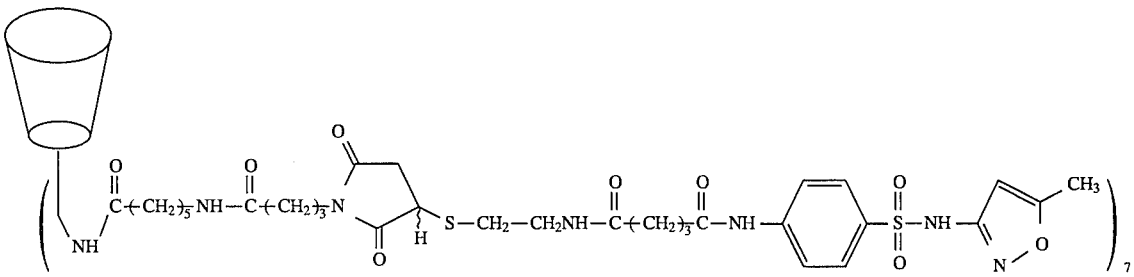

ybutanoyl)-sulfamethoxazole (Intermediate A(4), 0.35 g, 0.95 mmol or approximately a 3 fold molar excess relative Intermediate A(10): Hepta-[6- (γ-maleimido-n-butyryl-ε-aminocaproyl)amino]-β-cyclodextrin

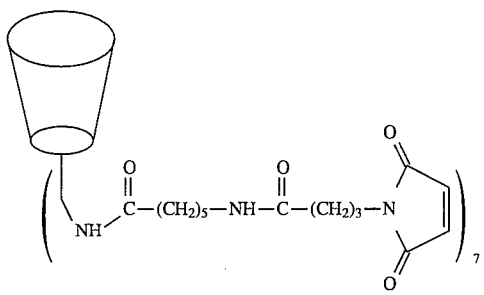

Hepta-[6-(ε-aminocaproyl)amino]-β-cyclodextrin heptahydrochloride (Compound 8, 0.5 g, 0.23 mmol) was dissolved in 60 mL of 0.1M ammonium carbonate and stirred at room temperature. To the stirring solution was added γ-maleimido-n-butyric acid N-hydroxysuccinimide ester (GMBS, 2.25 g, 8.03 mmol or approximately a 5 fold molar excess relative to the total amine content of the β-cyclodextrin sample) predissolved in 40 mL of tetrahydrofuran. The reaction mixture was stirred overnight at room temperature and then concentrated under reduced pressure to afford the crude product. This was purified by preparative reversed-phase HPLC or a Water Delta-Prep 3000 preparative chromatography system (47 mm×30 cm radial compression cartridge; 300Å 15 μm $C_{18}$; 20%–40% linear acetonitrile gradient containing 0.1% trifluoroacetic acid; 40 minutes; 100 mL/minute). Column fractions containing the product were combined, concentrated under reduced pressure and lyophilized to afford 251 mg (0.082 mmol, 36%) of product as a white amorphous solid. $^1$H-NMR (300 MHz, DMSO-$d_6$): δ 1.05–1.60 (m, 42H); 1.70 (m, 14H); 1.90–2.35 (m, 28H); 2.85–3.10 (m, 21H); 3.13–3.48 (m, 42H); 3.50–3.90 (m, 21H); 4.80 (br s, 7H); 7.00 (s, 14H); 7.77 (br t, 7H); 8.00 (br s, 7H).

FAB Mass Spectrum

Calculated MW+Na=3097

Found MW=3097

Amino acid analysis of this material confirmed the presence of equimolar quantities of ε-aminocaproic acid and γ-aminobutyric acid.

Compound 10: Hepta-[6-(γ-3'-(5-sulfamethoxazolylglutaramidoethylthio)-succinimido-n-butyryl-ε-aminocaproyl)amino]-β-cyclodextrin Hepta-[6-(γ-maleimido-n-butyryl-ε-aminocaproyl)amino]-β-cyclodextrin (Intermediate A(10), 100 mg, 32.5 μmol, 228 μmol total maleimide content) was dissolved in 10 ml of HEPES buffer (0.2M, pH 7.5) to afford a 10 mg/mL solution which was stirred at room temperature. To the stirring solution was added $N^4$-(5-cysteaminylglutaryl)-sulfamethoxazole (Intermediate B(5), 147 mg, 345 μmol or approximately a 1.5 fold molar excess relative to the total maleimide content of the β-cyclodextrin sample) and the reaction mixture then stirred overnight at room temperature. The product was partially purified/isolated by ultrafiltration against a 3,000 mwco membrane using several volume changes of phosphate-buffered saline, then endotoxin-free water. Final purification was carried out by preparative reversed-phase HPLC on a Waters Delta-Prep 3000 preparative chromatography system (47 mm×30 cm radial compression cartridge; 300Å 15 μm $C_{18}$; 0%–80% linear acetonitrile gradient containing 0.1% trifluoroacetic acid; 40 minutes; 100 mL/minute. Column fractions containing the product were combined, concentrated under reduced pressure and lyophilized to afford 60 mg (9.95 μmol, 31%) of compound 10 as a white, powdery solid.

Low Resolution Laser Desorportion Mass Spectrum

Calculated MW=6029

Found MW=6027 (within known 0.1% MW experimental error of instrumentation)

Amino acid analysis of this material confirmed the presence of 7 mol of sulfamethoxazole per mol of β-cyclodextrin.

Example 11

Octa-[(5-sulfamethoxazolylglutaramidoethylthio)acetyl]-Gly$_8$D-Lys$_4$Gly$_4$D-Lys$_2$Gly$_2$D-Lys-β-alanine amide

```
         R'                    R'
         |                     |
         Gly                   Gly
         |                     |
         D-Lys                 D-Lys
       /       \             /       \
      Gly      Gly         Gly       Gly
     /           \         /           \
   R'            D-Lys                  R'
                  |
                  Gly
                  |
                D-Lys(β-Ala)—CONH₂
                  |
                  Gly
                  |
   R'            D-Lys                  R'
     \           /         \           /
      Gly      Gly         Gly       Gly
       \      /             \       /
        D-Lys                 D-Lys
         |                     |
         Gly                   Gly
         |                     |
         R'                    R'
```

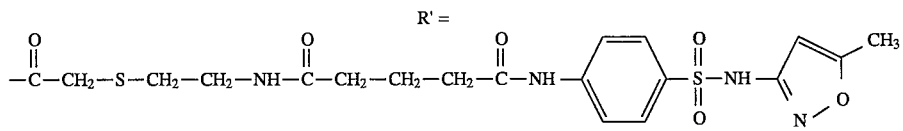

It will be appreciated that in this embodiment of the present invention X constitutes a part of the scaffold R and is not present as a separate addition.

Intermediate A(11): Octa-[bromoacetyl]-Gly$_8$D-Lys$_4$Gly$_4$D-Lys$_2$Gly$_2$D-Lys-β-alanine amide

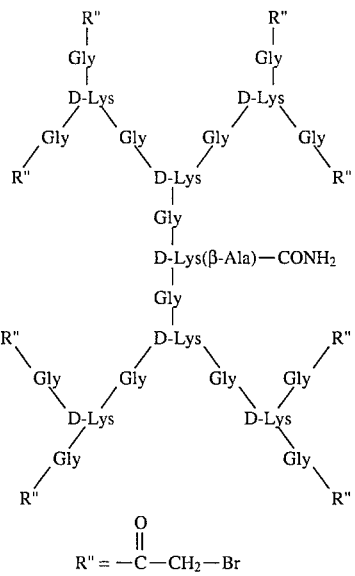

$$R'' = -\overset{O}{\underset{\|}{C}}-CH_2-Br$$

Intermediate A(11) was prepared by manual solid-phase peptide synthesis (0.5 mmol reaction scale) using dicyclohexyl/carbodiimide/1-hydroxybenzotriazole (DCC/HOBt) preactivation and commercially available methyl benzhydryl amine (MBHA)-resin. N-Tert-butyloxycarbonyl-protected glycine (Gly), D-lysine (D-Lys) and β-alanine (β-Ala) served as the protected amino acid derivatives. Although bromoacetylation of Gly$_8$D-Lys$_4$Gly$_4$D-Lys$_2$Gly$_2$D-Lys-β-alanine amide was readily accomplished in solution with bromoacetic anhydride, as a matter of convenience, bromoacetylation was carried out on the resin with bromoacetic anhydride (2 successive bromoacetylation reactions). The peptide was cleaved from the resin using hydrogen fluoride (HF) containing 10% anisole (as a cation scavenger) at 0° C. for 1 hour. The crude peptide was extracted into 10% acetic acid in water and purified by preparative reversed-phase HPLC on a Waters Delta-Prep 3000 preparative chromatography system (47 mm×30 cm radial compression cartridge; 300Å 15 μm C$_{18}$; 0%–80% linear acetonitrile gradient containing 0.1% trifluoroacetic acid; 40 minutes; 100 mL/minute). Column fractions containing the product were combined, concentrated under reduced pressure and lyophilized to afford 189 mg (0.068 mmol, 13.7%) of product as a white, fluffy solid.

Low Resolution Laser Desorption Mass Spectrum

Calculated MW+Na=2785

Found MW=2786 (within known 0.1% MW experimental error of instrumentation)

Amino acid analysis: Gly 14.27 (14); Lys 6.84 (7); β-Ala 0.89 (1).

Compound 11:

Octa-[(5-sulfamethoxazolylglutaramidoethylthio)acetyl]-Gly$_8$DLys$_4$Gly$_4$D-Lys$_2$Gly$_2$D-Lys-β-alanine amide Octa-[bromoacetyl]-Gly$_8$D-Lys$_4$Gly$_4$D-Lys$_2$Gly$_2$D-Lys-β-alanine amide (Intermediate A(11), 100 mg, 36.2 μmol, 290 μmol total bromoacetyl content) was taken up in 10 mL of HEPES buffer (0.2M, pH 7.5) containing 10% (v/v) tetrahydrofuran to afford a 10 mg/mL solution which was stirred at room temperature. To the stirring solution was added N$^4$-(5-cysteaminylglutaryl)-sulfamethoxazole (Intermediate B(5), 617 mg, 1.448 mmol or approximately a 5 fold molar excess relative to the total bromoacetyl content of the peptide sample) predissolved in 10 mL of HEPES/tetrahydrofuran (1:1, v/v). The resulting pH 7.65 reaction mixture was stirred at room temperature for 2 hours at which time analytical HPLC (C$_{18}$ reversed-phase) indicated the reaction to be complete. Dithiothreitol (DTT, 400 mg, 2.6 mmol) was then added and stirring continued for an additional 30 minutes to ensure complete reduction of any disulfide derived from N$^4$-(5-cysteaminylglutaryl)'sulfamethoxazole prior to HPLC purification.

Purification was carried out by preparative reversed-phase HPLC on a Waters Delta-Prep 3000 preparative chromatography system (47 mm×30 cm radial compression cartridge; 300Å 15 μm C$_{18}$; 0%–80% linear acetonitrile gradient containing 0.1% trifluoroacetic acid; 40 minutes; 100 mL/minute). Column fractions containing the product were combined, concentrated under reduced pressure and lyophilized to afford 30.3 mg (5.49 μmol, 15%) of compound 11 as a white, powdery solid.

Electrospray Mass Spectrum

Calculated MW=5522

Found MW=5517 (from manual deconvolution of +4 charge state in mass spectrum)

Amino acid analysis: Gly 14.53(14); Lys 7.14(7); β-Ala 1.02(1); amino acid analysis also confirmed the presence of 8 mol of sulfamethoxazole per mol of peptide.

Example 12

Effect of SMX-Size-Restricted Scaffold on Established Anti-SMX IgG Response

Figure 4:
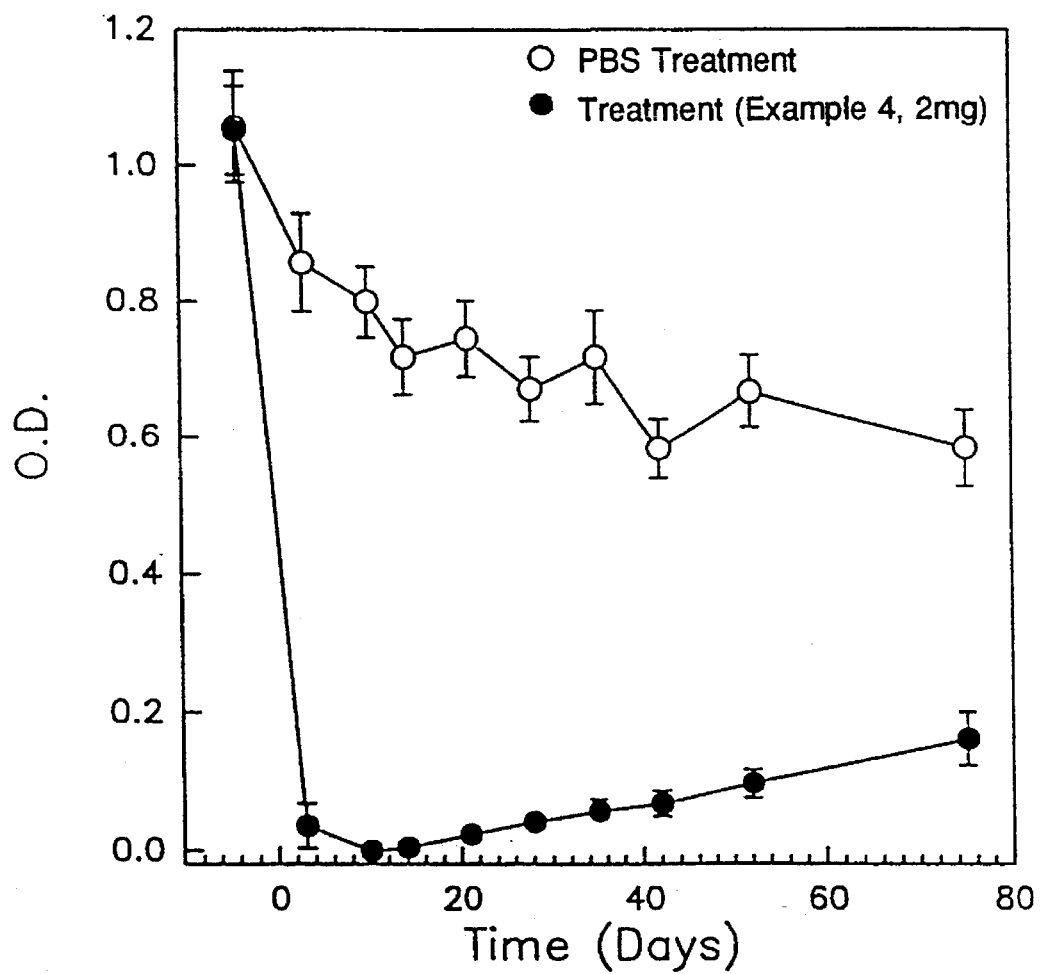
FIG. 4 shows the effect of treatment with SMX-size restricted scaffold on an established anti-SMX IgG antibody response in mice. Open circles designate PBS treatment while filled circles designate treatment (Example 4, 2mg).

Experiments in mice in which anti-SMX antibodies were induced using an SMX-protein carrier/adjuvant complex demonstrated that an anti-SMX antibody response can be abrogated or reduced. Anti-SMX antibodies were induced in Balb/c mice by immunization (either one or two injections) with 10 μg SMX conjugate (i.e., SMX covalently coupled to the protein keyhole limpet hemocyanin (=SMX-KLH)) adsorbed to 1 mg of aluminum hydroxide (alum) as adjuvant. Mice produced IgG antibodies to both the SMX and the protein carrier KLH, measured 3 weeks after immunization, and these antibody levels persisted for at least 8 weeks. After the anti-SMX response was established, groups of mice (8 per group) were treated with a single intraperitoneal injection of either phosphate-buffered saline (PBS) or 2 mg of a suppressive SMX-Dex construct (Example 4, 35 copies of SMX coupled to a dextran scaffold of 70,000 average molecular weight via an amide linking entity). The anti-SMX antibody levels in the saline treated animals remained high, but mice treated with the SMX-Dex construct (Example 4) lost their IgG antibodies to SMX for at least 2 weeks, and antibodies remained significantly suppressed for a further 60 days (see FIG. 4). Plotted are the mean IgG antibody levels +/− standard deviations. The antibody levels were measured in a standard enzyme-linked immunosorbent assay (ELISA), and expressed as optical density (O.D) units. The antibody levels to the protein carrier, KLH, remained unaffected by either treatment (data not shown).

Eighty days after treatment, the groups of mice were divided and half of each group re-treated with 2 mg of the SMX-Dex construct (Example 4). All the mice were then re-immunized (boosted) with SMX-KLH/alum, and 3 days later, the mice were killed, the spleens removed and the number of cells secreting anti-SMX IgG antibodies were enumerated. Results are shown in Table 1.

TABLE 1

Anti-SMX Antibody secreting cells per 100,000 spleen cells. Mean +/− standard deviation. SMX-Dex = Example 4.

| Group 1. | PBS/PBS | 57 +/− 20 |
|---|---|---|
| Group 2. | PBS/SMX-Dex | 9.75 +/− 4.9 |
| Group 3. | SMX-Dex/PBS | 4 +/− 2.1 |
| Group 4. | SMX-Dex/SMX-Dex | 1.25 +/− 0.96 |

It can be seen that mice in groups 2–4, which are groups treated with the SMX-Dex construct (Example 4), had many fewer specific antibody secreting cells in their spleens after a boosting immunization than PBS-treated controls, even if, as in the case of group 3, the SMX-Dex treatment was given 80 days before the boost.

Example 13

Effect of SMX-Size Restricted Scaffold on Anti-SMX IgE Antibody Levels

Figure 5A:
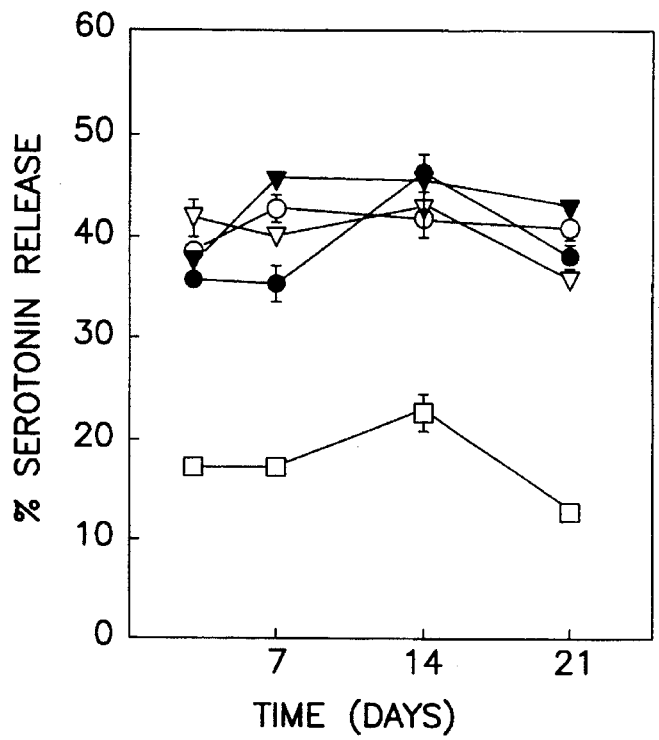
FIG. 5 shows the effect of treatment with SMX-size restricted scaffold on anti-SMX IgE antibody response in mice.
Figure 5B:
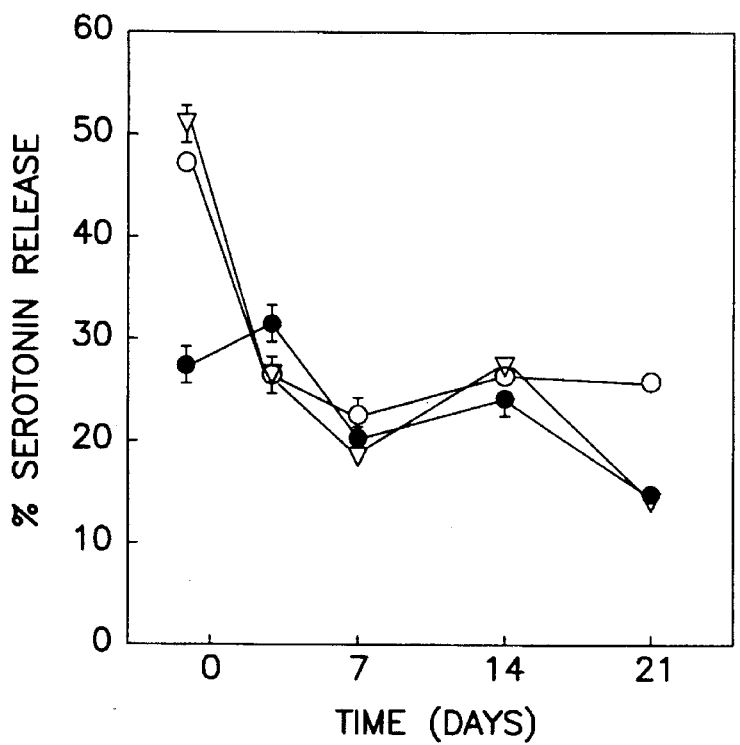

In another experiment, mice which had anti-SMX IgE antibodies C as well as anti-SMX IgG antibodies were similarly treated with either PBS or 2 mg of SMX-Dex (Example 5, 70,000 average molecular weight dextran with 44 copies of SMX covalently attached via a succinimide-based, thioether linking entity), and the IgE antibody levels measured up to 21 days after treatment (see FIG. 5).

The upper graph in FIG. 5 shows anti-SMX IgE antibody levels of individual mice treated only with PBS. The lower graph shows anti-SMX IgE antibody levels of individual mice treated with SMX-Dex (Example 5). IgE antibodies are measured by their ability to cause degranulation of a rat tissue culture mast cell line. These mast cells are pre-treated with the serum under investigation and radiolabelled serotonin. During this pre-treatment, IgE in the serum will bind to the high affinity IgE receptor on the cells, and serotonin will be incorporated into granules within the cell. On subsequent exposure to multivalent SMX (SMX coupled to bovine serum albumin), the specific IgE on the mast cells will be cross-linked and will cause the cells to degranulate. Under appropriate test conditions, the amount of radiolabelled serotonin released will be related quantitatively to the amount of IgE present in the test serum. Mice treated with SMX-Dex (Example 5), but not with PBS, showed loss of anti-SMX IgE antibodies up to 21.days after treatment (see FIG. 5).

Example 14

Intraperitoneal Versus Subcutaneous Administration

Figure 6:
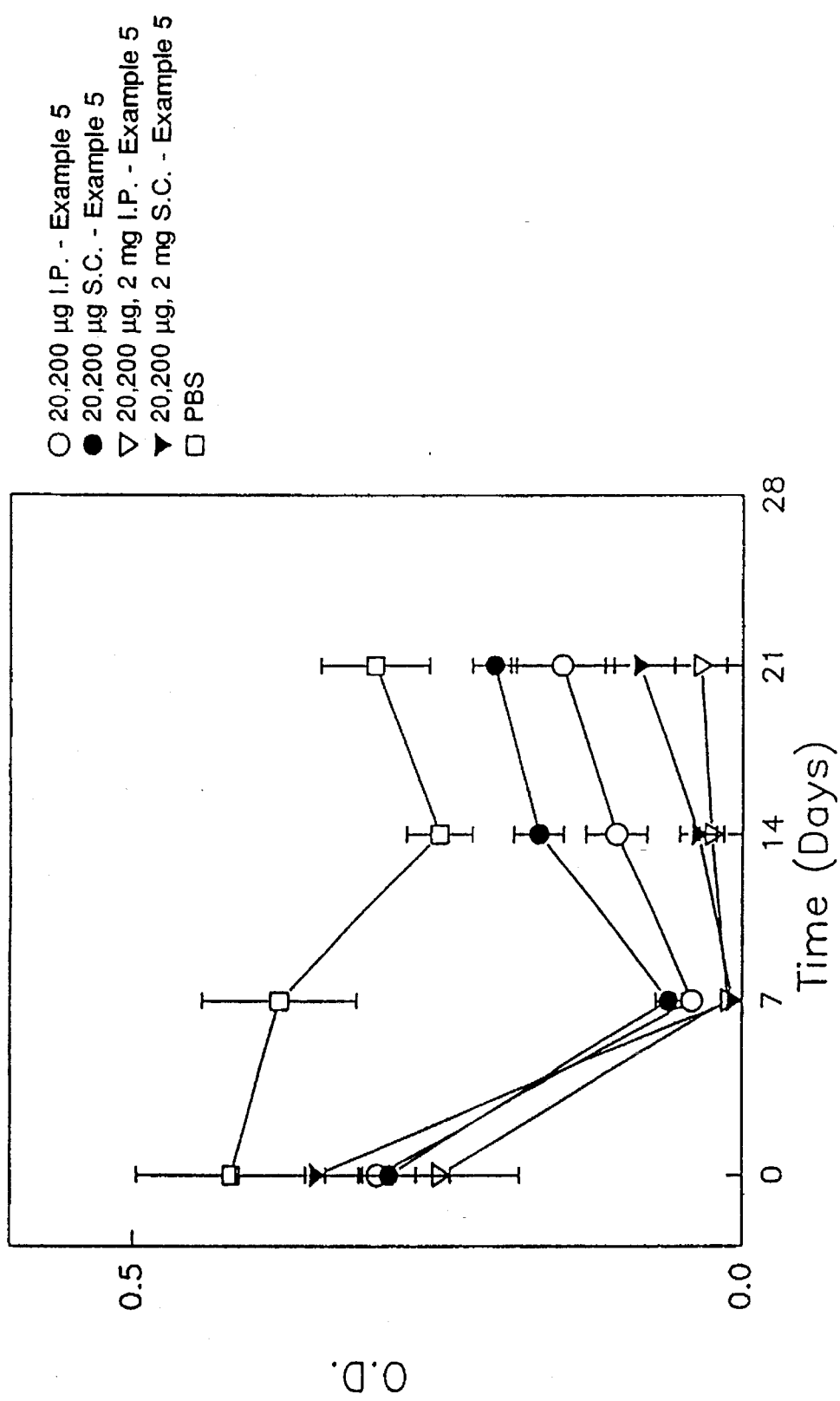
FIG. 6 shows the effect of intraperitoneal versus subcutaneous treatment with SMX-size restricted scaffold in mice. Open circles exemplify 20, 200 IP of Example 5. Filled circles exemplify 20, 200 S.C. of Example 5. Open triangles exemplify 20, 200, 2 mg S.C. in Example 5. Filled triangles exemplify 20, 200, 2 mg S.C. in Example 5. Open squares is for PBS.

Mice with pre-existing IgG against SMX could also be effectively treated with an SMX-Dex construct administered by the subcutaneous route. In such an experiment, immunized mice were treated with 2.22 mg or 0.22 mg of SMX-Dex (Example 5, 70,000 average molecular weight dextran with 62 copies of SMX covalently attached via a succinimide-based, thioether linking entity) given either by the intraperitoneal or subcutaneous route. Control mice were treated with PBS. Anti-SMX IgG antibody levels were measured up to 21 days (see FIG. 6).

Mice with pre-existing anti-SMX IgG, as measured by standard ELISA, lost these IgG antibody levels after treatment with 2.22 mg of SMX-Dex (Example 5, given as three injections one hour apart, of 20 µg, 200 µg, then 2 mg, of construct). Mice given a lower dose (20 µg, then 200 µg) of SMX-Dex (Example 5) showed a less complete cure. The route of injection (intraperitoneal versus subcutaneous) did not affect the ability of the construct to abrogate the antibody response. Shown are mean and standard deviation of O.D.

Example 15

Effect of Linker on Anti-SMX IgG Suppression

Figure 7:
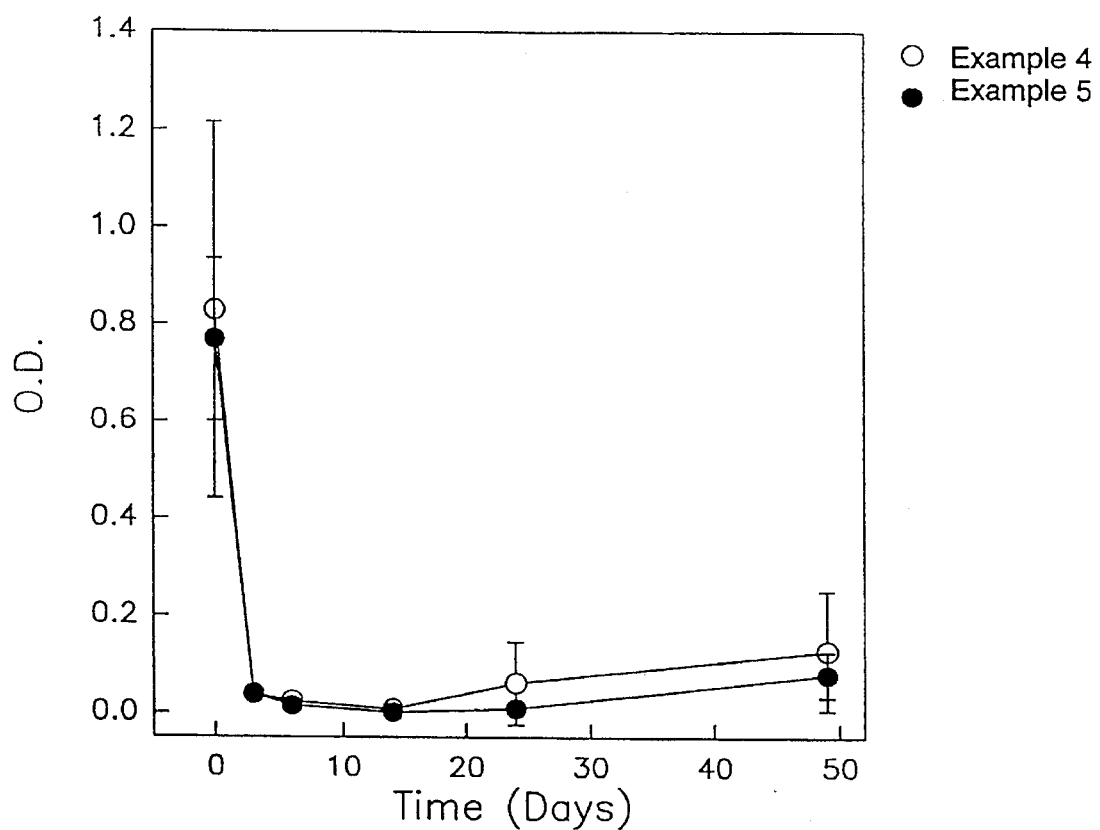
FIG. 7 shows the effect of various linking entities on the ability of SMX-size restricted scaffold to abrogate an anti-SMX IgG antibody response in mice. Open circle corresponds to Example 4 and filled circle corresponds to Example 5.

In another experiment, the effect of the nature of the linking entity used to covalently attach SMX to 70,000 average molecular weight dextran was investigated. Mice were immunized with SMX-KLH/alum as before and treated with either 2 mg of SMX-Dex Example 4 (35 copies of SMX linked via an amide linking entity). or 2 mg of SMX-Dex Example 5 (62 copies of SMX linked via a succinimide-based thioether linking entity), with PBS being administered to control mice. Serum IgG antibody levels were measured up to 49 days. It can be seen that both constructs are equally effective in suppressing the anti-SMX IgG antibody response (see FIG. 7).

Shown are mean and standard deviation of O.D. representing IgG antibody levels in 2 groups of mice, one treated with 2 mg of SMX-Dex Example 4 and one treated with 2 mg of SMX-Dex Example 5 intraperitoneally. There is no significant difference between the groups.

Example 16

Prevention of Anti-SMX IgG Antibody Response

Treatment of mice with an SMX-size restricted scaffold construct before or just after immunization prevents the IgG antibody response to immunization with SMX-KLH/alum. In such an experiment, mice were treated with either PBS, or with 0.5 mg or 2.0 mg of SMX-Dex (Example 6, 40,000 average molecular weight dextran with 14 copies of SMX covalently attached via a succinimide-based, thioether linking entity). The treatments were given on the day before, day of, or the day after, immunization with 10 µg of SMX-KLH/alum. Table 2 shows anti-SMX IgG antibody levels measured 30 days later.

TABLE 2

| Treatment (SMX-Dex = Example 6) | Anti-SMX IgG levels measured 30 days after immunization Mean O.D. +/− standard deviation |
|---|---|
| Day before immunization | |
| PBS | 0.584 +/− 0.186 |
| SMX-Dex | 0.021 +/− 0.011 |
| SMX-Dex 2.0 mg | 0.018 +/− 0.007 |
| Day of immunization | |
| PBS | 0.823 +/− 0.25 |
| SMX-Dex 0.5 mg | 0.017 +/− 0.013 |
| SMX-Dex 2.0 mg | 0.028 +/− 0.026 |
| Day after immunization | |
| PBS | 0.715 +/− 0.212 |
| SMX-Dex 0.5 mg | 0.105 +/− 0.057 |
| SMX-Dex 2.0 mg | 0.029 +/− 0.026 |

It can be seen that the group of mice treated with PBS has clearly measurable anti-SMX antibodies on day 30 after immunization, while SMX-Dex (Example 6)-treated mice made significantly less, or no anti-SMX antibodies.

Example 17

Valence-Restricted Scaffold: Effect on Anti-SMX IgG Antibody Response

Mice may also be treated prophylactically with an SMX-specific immunosuppressive agent derived from a valence-restricted, peptide-based dendritic scaffold (PBD) to prevent immunization with the immunogenic SMX-KLH/alum.

In such an experiment, mice were treated subcutaneously the day before immunization with the following: (1) PBS, (2) SMX-Dex (Example 6, 40,000 average molecular weight dextran with 14 copies of SMX covalently attached via a succinimide-based, thioether linking entity) at 2.0 mg or 0.5mg, (3) SMX-PBD (Example 11, a peptide-based, dendritic scaffold with 8 copies of SMX covalently attached via a non-succinimide-based, thioether linking entity), (4) SMX monomer (Intermediate A(4), SMX chemically blocked to prevent attachment to itself or other entities). The SMX-PBD (Example 11) and SMXmonomer (Intermediate A(4)) doses were adjusted to give molar amounts of SMX equivalent to that present in the SMX-Dex construct (Example 6). IgG antibody levels were measured at intervals up to 33 days post immunization.

Figure 8:
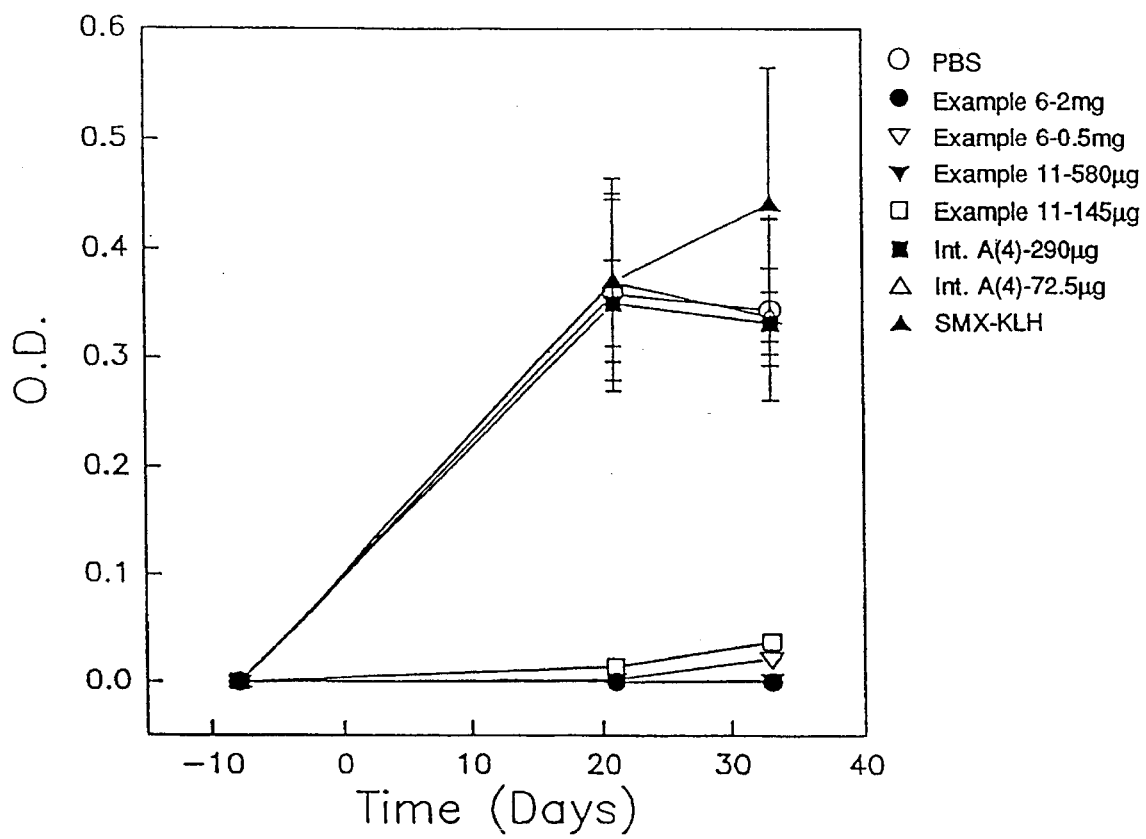
FIG. 8 shows the prevention of an anti-SMX IgG antibody response in mice with SMX-valence restricted scaffold after immunization.

It can be seen that both SMX-Dex (Example 6) and SMX-PBD (Example 11) constructs-prevented an anti-SMX IgG antibody response from forming after immunization with SMX-KLH/alum. In contrast, mice treated with PBS or with monomeric SMX (Intermediate A(4)) made a good anti-SMX IgG response after immunization (see FIG. 8). Shown are mean and standard deviation of O.D. measurements representing IgG levels in groups of mice pretreated intraperitoneally with either SMX-Dex (Example 6), SMX-PBD (Example 11) or SMX monomer (Intermediate A(4)). Both types of multivalent SMX constructs prevented formation of an anti-SMX IgG response.

Example 18

β-Cyclodextrin: Prevention of Anti-SMX IgG Antibody Response

In a further experiment, another valence-restricted scaffold, namely, one based on β-cyclodextrin, was used to prevent an IgG antibody response from forming after immunization with SMXKLH/alum. In this experiment, mice were treated with PBS, 2 mg or 0.5 mg of SMX-Dex (Example 5, 70,000 average molecular weight dextran with 62 copies of SMX covalently attached via a succinimide-based, thioether linking entity), or the molar equivalent of SMX covalently coupled to β-cyclodextrin (SMX-βCD, Example 10, 7 copies of SMX attached via a succinimide-based, thioether linking entity). The mice were treated subcutaneously with the SMX-specific immunosuppressive agent or PBS one day before immunization with 10 μg SMX-KLH on 1 mg alum. The anti-SMX IgG antibody levels of these mice were measured 7 and 14 days after immunization. Results are shown in Table 3.

TABLE 3

Anti-SMX IgG antibody levels in control and treated mice (mean O.D. +/− standard deviation) SMX-Dex = Example 5; SMX-βCD = Example 10.

| Treatment after | IgG 7 days after immunization | IgG 14 days after immunization |
|---|---|---|
| PBS | 0.843 +/− 0.1 | 1.006 +/− 0.118 |
| SMX-Dex 2.0 mg | 0.002 +/− 0.011 | 0.008 +/− 0.006 |
| SMX-Dex 0.5 mg | 0.055 +/− 0.021 | 0.159 +/− 0.031 |
| SMX-βCD 1.49 mg | 0.082 +/− 0.027 | 0.067 +/− 0.020 |
| SMX-βCD 0.37 mg | 0.139 +/− 0.055 | 0.125 +/− 0.045 |

It can be seen that, like pretreatment with SMX-Dex (Example 5), pretreatment with SMX covalently attached to the valence-restricted scaffold β-cyclodextrin (Example 10) prevented the formation of a significant anti-SMX IgG antibody response 14 days after immunization.

Example 19

SMX-Scaffold Constructs Function in More Than One Mammalian Species

Both abrogation of pre-existing anti-SMX IgG antibody levels and prevention of the formation of an antibody response may be effected by SMX-scaffold constructs in species other than mice, namely, rats.

Figure 9:
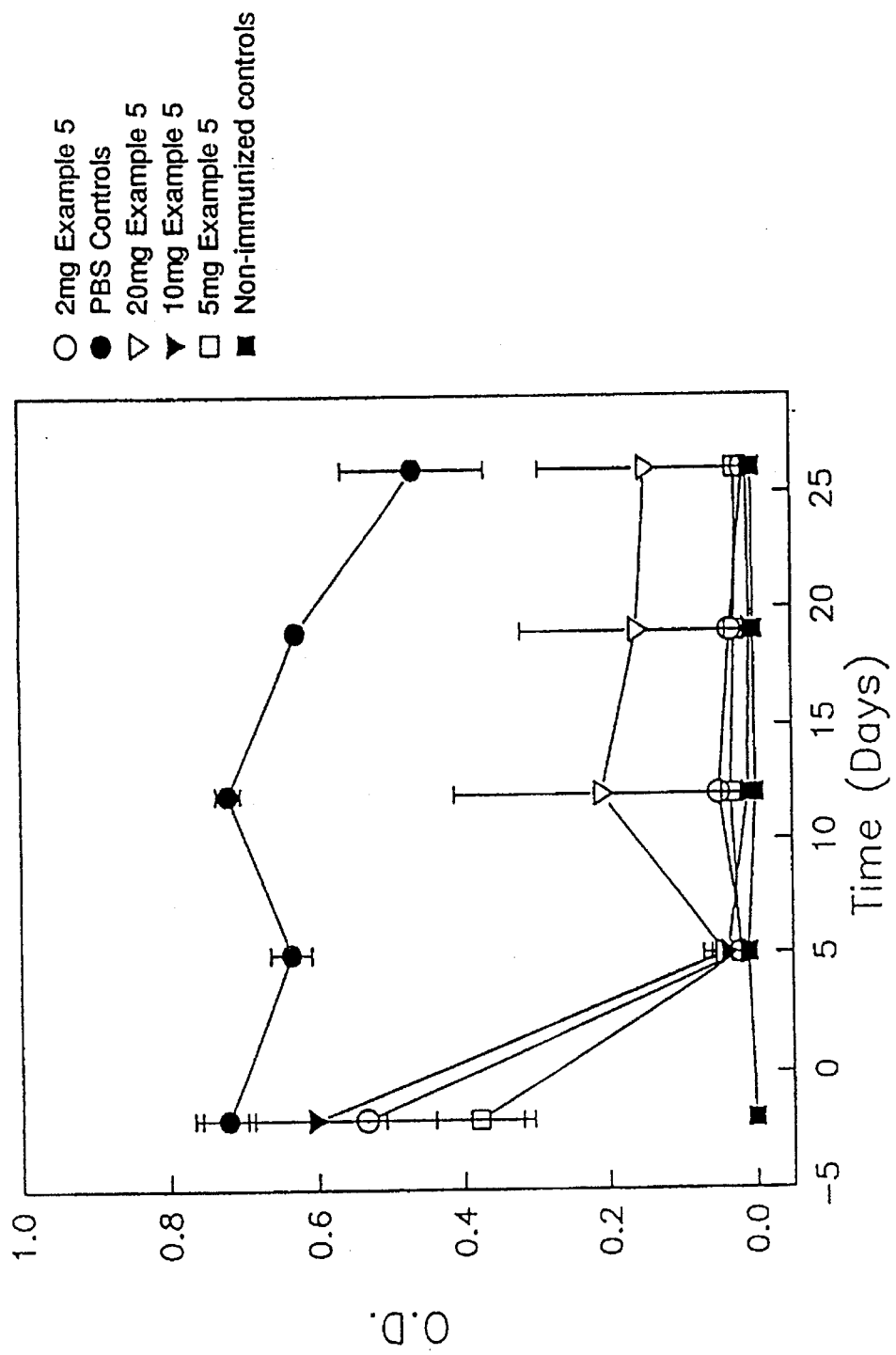
FIG. 9 shows the abrogation of an anti-SMX IgG antibody response in rats treated with various doses of SMX-size restricted scaffold.

In one experiment, rats were immunized with 25 μg SMX-KLH on 2 mg alum, intraperitoneally. Thirty nine (39) days later, at which time a good anti-SMX IgC response was established, rats were treated intraperitoneally with either PBS, or the following doses of SMX-Dex (Example 5, 62 copies of SMX covalently attached to 70,000 average molecular weight dextran via a succinimide-based, thioether linking entity): 2.0 mg, 5.0 mg, 10 mg or 20 mg. IgG antibody levels were measured up to 26 days after treatment. The results are shown in FIG. 9. Shown are means and standard deviations of O.D. measurements representing the IgG antibody level to SMX in groups of rats treated intraperitoneally with different doses of SMX-Dex (Example 5). It can be seen that treatment with all doses of SMX-Dex (Example 5) abrogated anti-SMX IgG, while PBS-treated controls maintained their anti-SMX antibodies.

In a second experiment, rats were pretreated subcutaneously with either PBS or SMX-Dex (Example 6, 22 copies of SMX covalently attached to 40,000 average molecular weight dextran via a succinimide-based, thioether linking entity). The doses used were 0.5 mg, 2.0 mg or 5.0 mg. The following day, the rats were immunized with 25 μg SMX-KLH/alum. Anti-SMX IgG antibodies were measured 7 and 17 days after immunization. Results are shown in Table 4.

TABLE 4

Anti-SMX IgG antibody levels in control and treated rats (mean O.D +/− standard deviation) SMX-Dex = Example 6

| Treatment | 7 days after immunization | 17 days after immunization |
|---|---|---|
| PBS | 1.245 +/− 0.349 | 1.991 +/− 0.328 |
| 0.5 mg SMX-Dex | 0.181 +/− 0.082 | 0.118 +/− 0.038 |
| 2.0 mg SMX-Dex | 0.186 +/− 0.166 | 0.064 +/− 0.032 |
| 5.0 mg SMX-Dex | 0.065 +/− 0.032 | 0.026 +/− 0.026 |

All rats treated with the SMX-Dex construct (Example 6) one day before immunization made very low or no anti-SMX IgG antibody 17 days later, while control rats treated with PBS made good antibody responses.

Example 20

Multivalent SMX Constructs Cause Degranulation of Mast Cells and Release of Vasoactive Mediators Rat basophilic leukemia cells, a tissue culture tumor cell line with the characteristics of a mast cell, were pretreated overnight with radiolabelled serotonin and mouse serum containing anti-SMX IgE antibodies. At the end of the incubation time, the IgE had bound to the high affinity IgE receptor on these cells and the radiolabelled serotonin was incorporated into the secretory granules present in the cells. The cells had thus been rendered analogous to skin mast cells in an individual making an IgE response to SMX. The cells were then washed and exposed to SMX in the following forms:

1. Monovalent SMX (Intermediate A(4))
2. 40,000 average molecular weight dextran with 22 copies of SMX covalently attached via a succinimide-based, thioether linking entity (Example 6)
3. 70,000 average molecular weight dextran with 44 copies of SMX covalently attached via a succinimide-based, thioether linking entity (Example 5)
4. β-Cyclodextrin with 7 copies of SMX covalently attached via a succinimide-based, thioether linking entity (Example 10)

Figure 10:
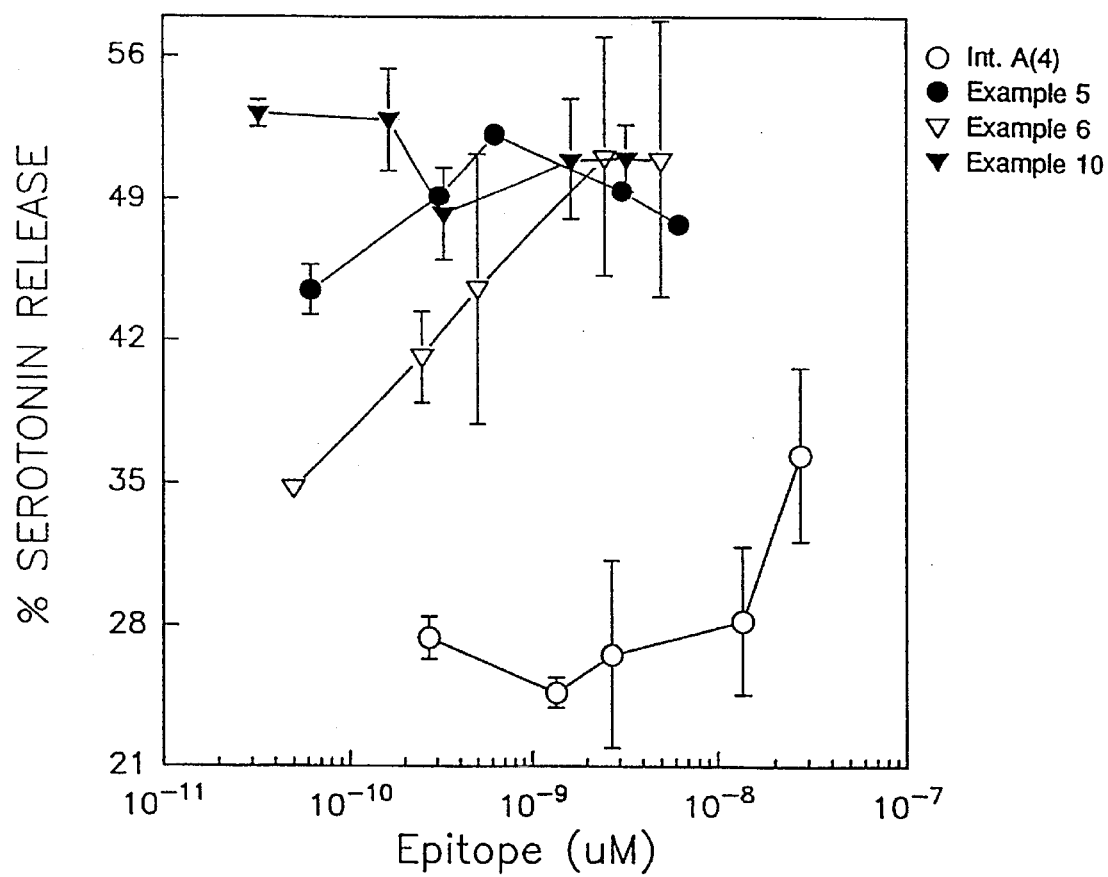
FIG. 10 shows degranulation of mast cells following exposure to SMX constructs.

It can be seen from FIG. 10 that the multivalent arrays of SMX are much more efficient than monovalent SMX at inducing serotonin release from the IgE-loaded mast cells, i.e., at least 3 orders of magnitude higher concentrations of monomer are required to induce the same amount of serotonin release. It may be expected, therefore, that multivalent SMX constructs, based on both size- and valence-restricted scaffolds, will be much more reliable and efficient than monovalent SMX at inducing diagnostic wheal and flare reactions in the skin of individuals who have already made IgE antibodies to the drug.

Example 21

SMX-Size Restricted Scaffold Construct Can Effect a Positive Skin Test in Rat Skin Passively Sensitized with Anti-SMX IgE Three naive male Sprague-Dawley rats were anesthetized, a catheter positioned in the jugular vein and the dorsal surface depilated. Intradermal injections of 50 μL of the following were then made:

(A) Anti-SMX IgE-containing mouse serum at 1: 10, 1: 100 and 1: 1000 dilutions.
(B) Anti-dinitrophenol (DNP) monoclonal IgE antibody at 100 μg/ml, 10 μg/ml and 1 μg/ml.
(C) Compound 48/80 at 1μg/ml PBS. (This is a mast cell degranulator commercially available from Sigma Chemical Company.)

Figure 11A:
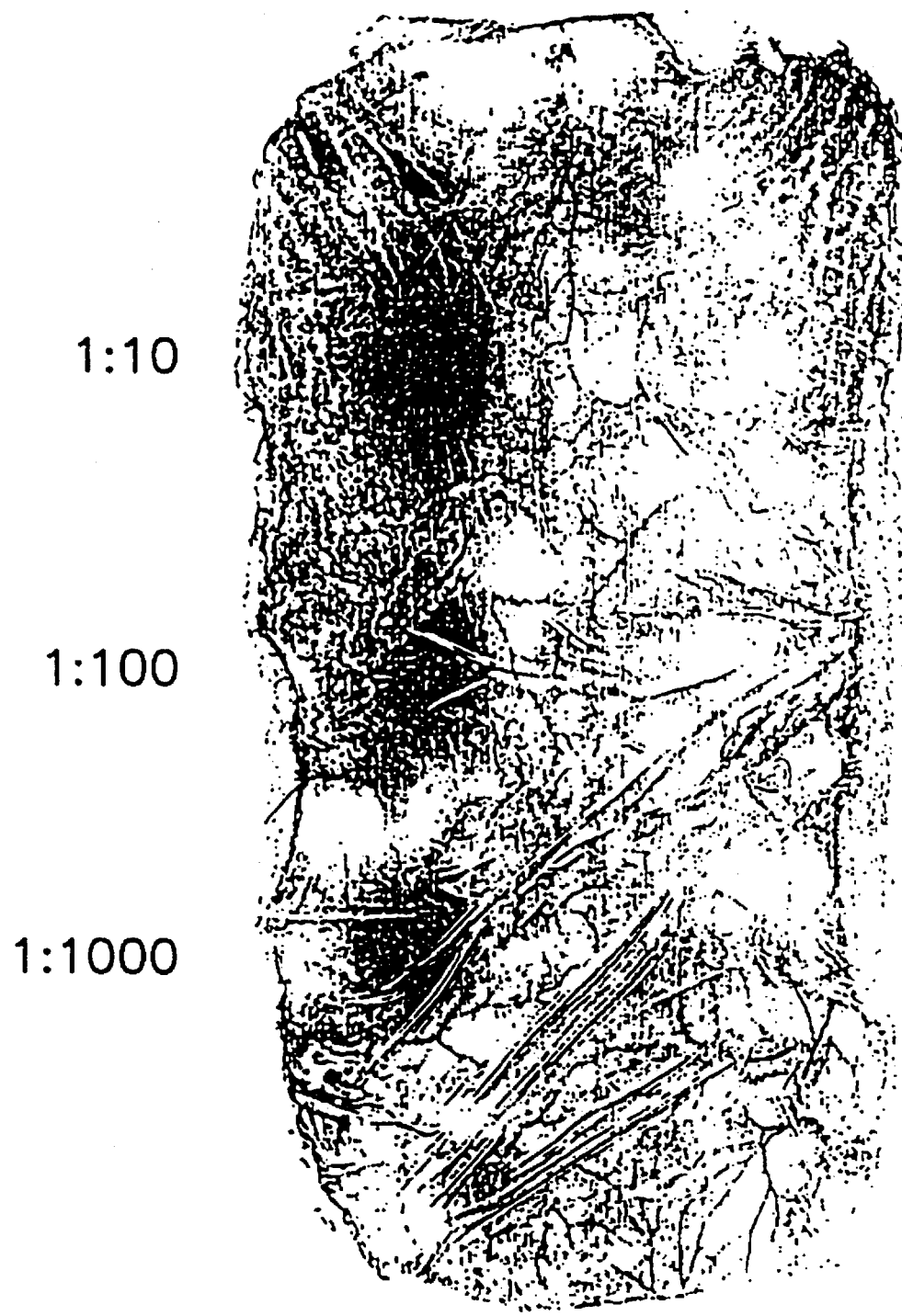
FIG. 11 shows positive wheal and flare reaction in rat skin after anti-SMX IgE on the skin mast cells has been cross-linked with multivalent SMX-size restricted scaffold.
Figure 11B:
Figure 11C:
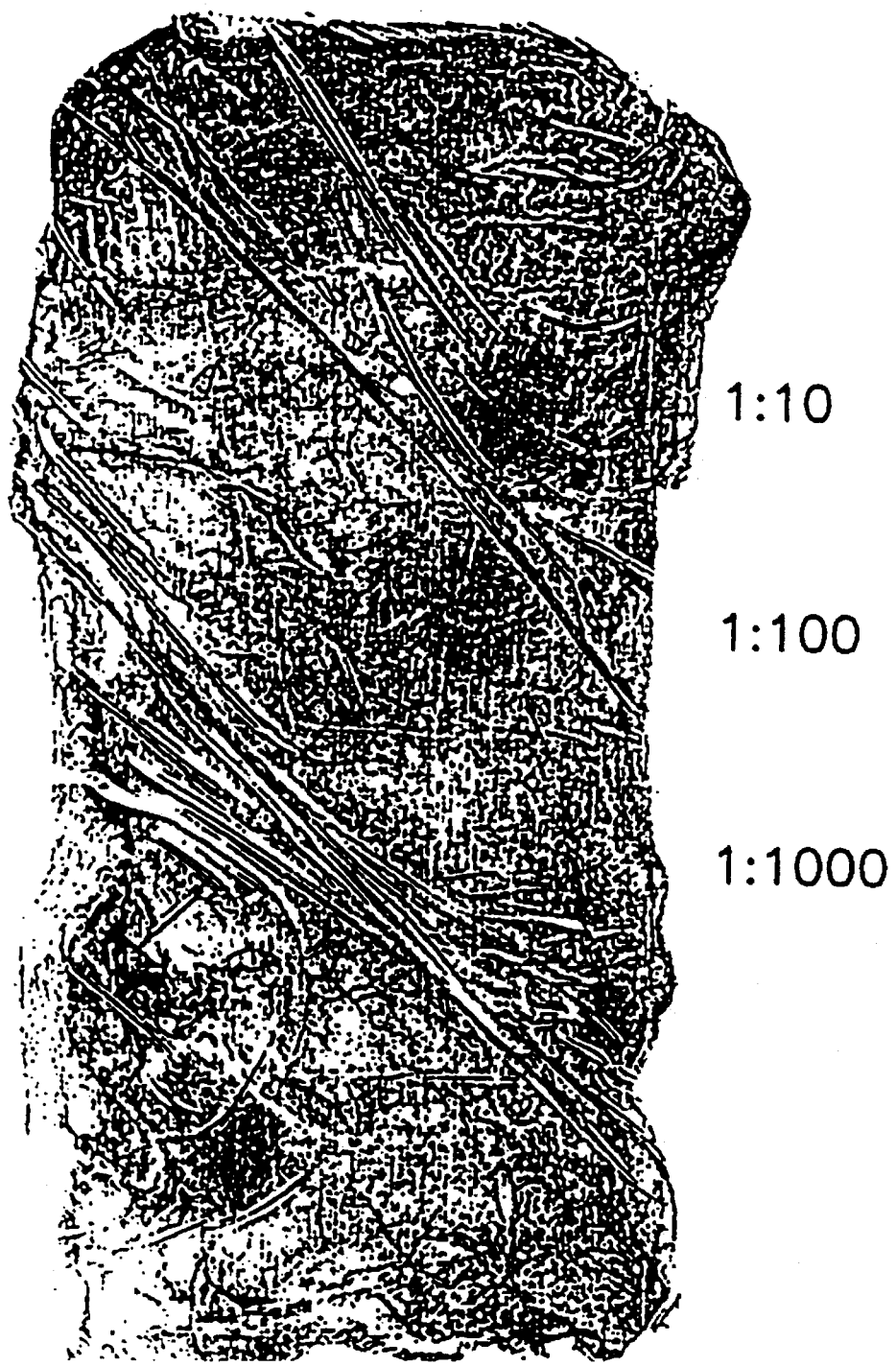

After a delay of 1 hour, the rats were injected intravenously with Evans Blue dye at 30 mg/kg. After a further 15 minute delay, 2 of the 3 rats received 1 mg/kg SMX-Dex (Example 5, 62 copies of SMX covalently attached to 70,000 average molecular weight dextran via a succinimide-based, thioether linking entity), and one rat received 1 mg/kg DNP-bovine serum albumin as a multivalent version of DNP. Thirty (30) minutes later, rats were killed and the dorsal skin removed. FIG. 11 shows the result. Sites of mast cell degranulation in the skin were clearly visible as dark spots, caused by extravasation of Evans blue dye from capillaries made leaky by released mast cell mediators. Anti-DNP IgE was injected into sites on the left hand side of the skins, anti-SMX IgE on the right. It can be seen in (FIG. 11A) which received an intravenous injection of multivalent DNP, that all three dilutions of the anti-DNP IgE gave rise to positive skin reactions, while the anti-SMX IgE sites remained negative. In (FIGS 11B and 11C, respectively), which received an intravenous injection of multivalent SMX (SMX-Dex Example 5, 62 copies of SMX covalently attached to 70,000 average molecular weight dextran via a succinimide-based, thioether linking entity), the anti-DNP IgE sites remained negative while the anti-SMX IgE sites showed positive reactions at the two highest concentrations. The PBS sites were negative, and the 48/80 sites were positive, as expected, in all three rats.

From these data one may predict that, in an individual with specific IgE to SMX, exposure of skin mast cells to SMX-Dex or other multivalent SMX constructs will cause local degranulation and a positive wheal and flare reaction, thus allowing the SMX-constructs to act as diagnostics for IgE status of patients.

Because of their multivalent nature, the agents of the present invention may be used as testing reagents for determining the IgE antibody status of individuals by intradermal or prick testing. The agents would be administered subcutaneously and the injection sites monitored for the classic wheal and flare reaction.

The agents of the present invention may also be used as reagents in a variety of solid phase or solution phase in vitro immunoassays for the determination of all classes of antibody, namely IgG, IgM, IgD, IgA and IgE. Such assays may include, although not be limited to: ELISA, Radioimmune assay (RIA), radioallergosorbent (RAST) and optical immunoassay (OIA).

We claim:

1. A compound of the formula

R—[X—Y—Z]$_n$ where
R is dextran of average molecular weight of about 10K to about 70K;
X is —OCH$_2$C(O)NH(CH$_2$)$_p$NH— where p is 2–8;
Y is —C(O)(CH$_2$)$_3$C(O)N(H)—;
Z is and n is a whole number from 2 to about 70.

2. A compound according to claim 1 wherein said dextran is of average molecular weight of about 10K.
3. A compound according to claim 2 wherein p is 2; and n is about 20 to about 50.
4. A pharmaceutically acceptable salt of the compound of claim 1.
5. A pharmaceutical composition for treating an undesired immune response to compositions containing sulfamethoxazole comprising an effective amount of the compound of claim 1 in a pharmaceutically acceptable carrier.
6. A method for treating an individual for an undesired immune response to compositions containing sulfamethoxazole comprising administering a therapeutically effective amount of the compounds of claim 1 to the individual.
7. A method of prophylactically treating an individual for an undesired immune response to compositions containing sulfamethoxazole comprising administering a therapeutically effective amount of the compounds of claim 1 to the individual.

* * * * *